(12) United States Patent
Scheg et al.

(10) Patent No.: US 11,623,018 B2
(45) Date of Patent: Apr. 11, 2023

(54) PHOTOACTIVATED SEMICONDUCTOR PHOTOCATALYTIC AIR PURIFICATION

(71) Applicant: Promethium Limited, Henderson, NV (US)

(72) Inventors: Devon Paul Scheg, Las Vegas, NV (US); Xavier Isaiah Morgan-Lange, North Las Vegas, NV (US)

(73) Assignee: PROMETHIUM LIMITED, Henderson, NV (US)

( * ) Notice: Subject to any disclaimer, the term of this patent is extended or adjusted under 35 U.S.C. 154(b) by 79 days.

(21) Appl. No.: 17/220,768

(22) Filed: Apr. 1, 2021

(65) Prior Publication Data
US 2022/0062489 A1 Mar. 3, 2022

Related U.S. Application Data

(63) Continuation-in-part of application No. 17/007,341, filed on Aug. 31, 2020.

(51) Int. Cl.
*A61L 9/20* (2006.01)
*B01J 35/00* (2006.01)
(Continued)

(52) U.S. Cl.
CPC .............. *A61L 9/205* (2013.01); *A61L 9/22* (2013.01); *B01J 23/31* (2013.01); *B01J 27/1817* (2013.01);
(Continued)

(58) Field of Classification Search
CPC .... B01J 23/31; B01J 27/1817; B01J 35/0033; B01J 35/004; B01J 37/345; A61L 9/205;
(Continued)

(56) References Cited

U.S. PATENT DOCUMENTS

| 5,872,072 A | 2/1999 | Mouri et al. |
| 9,469,906 B2 | 10/2016 | Irvine et al. |

(Continued)

FOREIGN PATENT DOCUMENTS

| CN | 2767877 | * 3/2006 | ............... F24F 3/16 |
| CN | 101940937 | 1/2011 | |

(Continued)

OTHER PUBLICATIONS

M. Zalfani, et al., "Novel 3DOM BiVO4/TiO2 nanocomposites for highly enhanced photocatalytic activity," J. Mater. Chem. A, 2015, 3, pp. 21244-21256 and 1-3.

(Continued)

*Primary Examiner* — Patricia L. Hailey
(74) *Attorney, Agent, or Firm* — Snell & Wilmer L.L.P.

(57) ABSTRACT

In various embodiments, an air purifier capable of destroying and deactivating airborne contaminants such as SARS-CoV-2 is described. The air purifier comprises a photocatalytic system comprising at least one photoactivated semiconductor photocatalyst and a lamp configured to irradiate and excite the at least one photoactivated semiconductor photocatalyst to generate reductive and/or oxidative reactive species from oxygen and/or water on the photocatalyst surface. In various embodiments, the photocatalytic system comprises a stack of PCB cards, each card having a photocatalytic layer disposed thereon, or a 3-dimensionally ordered macroporous (3-DOM) structure comprising an open cell lattice.

25 Claims, 7 Drawing Sheets

(51) Int. Cl.

| | | |
|---|---|---|
| *B01J 27/18* | (2006.01) | |
| *B01J 23/31* | (2006.01) | |
| *B01J 37/34* | (2006.01) | |
| *A61L 9/22* | (2006.01) | |
| *H01T 23/00* | (2006.01) | |
| *H01J 61/20* | (2006.01) | |

(52) U.S. Cl.
CPC ......... *B01J 35/004* (2013.01); *B01J 35/0033* (2013.01); *B01J 37/345* (2013.01); *H01T 23/00* (2013.01); *A61L 2209/12* (2013.01); *A61L 2209/14* (2013.01); *A61L 2209/16* (2013.01); *A61L 2209/211* (2013.01); *H01J 61/20* (2013.01)

(58) Field of Classification Search
CPC .... A61L 9/22; A61L 2209/12; A61L 2209/14; A61L 2209/16; A61L 2209/211; H01T 23/00; H01J 61/20
USPC .......................... 422/4; 435/235.1; 588/249.5
See application file for complete search history.

(56) References Cited

U.S. PATENT DOCUMENTS

| | | | |
|---|---|---|---|
| 9,947,816 | B2 | 4/2018 | Ardo et al. |
| 10,471,170 | B2 | 11/2019 | Lee |
| 10,683,218 | B2 | 6/2020 | Li |
| 2004/0258581 | A1 | 12/2004 | Wie et al. |
| 2009/0280027 | A1 | 11/2009 | Hayman, Jr. |
| 2013/0168228 | A1 | 7/2013 | Ozin et al. |
| 2015/0238644 | A1* | 8/2015 | Sung ...................... B01J 35/004 422/187 |
| 2015/0306271 | A1* | 10/2015 | Willette ............. B01D 53/8687 422/119 |
| 2016/0015848 | A1 | 1/2016 | Jung et al. |
| 2017/0224865 | A1* | 8/2017 | Ronda ..................... A61L 9/205 |
| 2017/0291170 | A1 | 10/2017 | Sambandan et al. |
| 2017/0370012 | A1 | 12/2017 | Ono et al. |
| 2019/0270075 | A1 | 9/2019 | Shayko et al. |
| 2020/0129972 | A1 | 4/2020 | Ozaki et al. |
| 2020/0131645 | A1 | 4/2020 | Suto et al. |
| 2020/0176654 | A1 | 6/2020 | Kim et al. |
| 2021/0346120 | A1* | 11/2021 | Roberts ..................... A61L 9/20 |

FOREIGN PATENT DOCUMENTS

| | | | | |
|---|---|---|---|---|
| CN | 106994343 | | 8/2017 | |
| CN | 108452362 | | 8/2018 | |
| JP | H1033990 | | 2/1998 | |
| JP | 2002319494 | | 10/2002 | |
| JP | 3649241 | | 5/2005 | |
| JP | 2009078211 | | 4/2009 | |
| JP | 5369210 | | 12/2013 | |
| JP | 2015067478 | | 4/2015 | |
| JP | 5754893 | B2 * | 7/2015 | ............. B01J 35/02 |
| KR | 100460255 | B1 * | 12/2004 | ............. A61L 9/205 |
| KR | 20050123067 | A * | 12/2005 | ............. B01D 39/20 |
| KR | 102027031 | | 11/2019 | |
| KR | 102074872 | | 12/2019 | |
| WO | 2005082491 | | 9/2005 | |
| WO | WO-2010120730 | A1 * | 10/2010 | ............. A62B 23/02 |
| WO | 2017055094 | | 4/2017 | |
| WO | 2017147995 | | 9/2017 | |

OTHER PUBLICATIONS

P. Zhou, et al., "All-Solid-State Z-Scheme Photocatalytic Systems," Adv. Mater., 2014, 26, 4920-4935.

O. Monfort, et al., "Bismuth vanadate-based semiconductor photocatalysts: a short critical review on the efficiency and the mechanism of photodegradation of organic pollutants," Environ. Sci. Pollut. Res. Int., Jul. 2018;25(20): 19362-19379.

J. Ke, et al., "Nanostructured Ternary Metal Tungstate-Based Photocatalysts for Environmental Purification and Solar Nater Splitting: A Review," Nano-Micro Lett., (20118) 10:69.

S. Lattante, "Electron and Hole Transport Layers: Their Use in Inverted Bulk Heterojunction Polymer Solar Cells," Electronics, 2014, 3, 132-164.

G. Collins, et al., "2D and 3D photonic crystal materials for photocatalysis and electrochemical energy storage and conversion," Science and Technology of Advanced Materials, 2016, vol. 17, No. 1, pp. 563-582.

Y. Jia, et al., "Highly efficient $(BiO)_2CO_3$—$BiO_{2-x}$-graphene photocatalysts: Z-Scheme photocatalytic mechanism for their enhanced photocatalytic removal of NO," Applied Catalysis B: Environmental/ Jan. 2019, pp. 241-252.

Xu, et al., Direct Z-scheme photocatalysts: Principles, synthesis, and applications, Materials Today d vol. 21, No. 10 d Dec. 2018, pp. 1042-1063.

Yang, et al., Preparation and photocatalytic properties of visible light driven Ag\AgBr/attapulgite nanocomposite, Applied Clay Science 67-68 (2012), pp. 11-17.

Zhou, et al., Construction of a metallic silver nanoparticle-decorated bismuth oxybromide-based composite material as a readily recyclable photocatalyst, Journal of Cleaner Production, https://doi.org/10.1016/j.jclepro 2019.119007.

Tang, et al., Construction of $Ag_3PO_4$/$Ag_2MoO_4$ Z-scheme heterogeneous photocatalyst for the remediation of organic pollutants, Chinese Journal of Catalysis 38 (2017) 337-347.

J. Pignatello, et al., "Advanced oxidation processes for organic contaminant destruction based on the Fenton reaction and related chemistry," Critical Review in Environmental Science and Technology, 2006, vol. 36, pp. 1-84.

R. Nakano, et al., "Broad spectrum microbicidal activity of photocatalysts by $TiO_2$," Catalysts, 2013, vol. 3, pp. 310-323.

S. Khaiboullina, et al., "Inactivation of human coronavirus by titania nanoparticle coatings and UVC radiation: Throwing light on SARS-CoV-2," Viruses, 2012, vol. 13, No. 19, pp. 1-15.

G. LiPuma, et al., "Kinetics rate model of the photocatalytic oxidation of trichloroethylene in air over $TiO_2$ thin films," Separation and Purification Technology, 2009, vol. 67, pp. 226-232.

T. Ming, et al., "Nitrous oxide could be removed from the atmosphere with simultaneous generation of renewable energy," Science for Environmental Policy, European Commission DG Environment News Alert Service, Nov. 11, 2016, Issue 476.

H. Foster, et al., "Photocatalytic disinfection using titanium dioxide: spectrum and mechanism of antimicrobial activity," Appl. Microbiol Biotechnol, 2011, vol. 90, pp. 1847-1868.

D. Gerrity, et al., "Photocatalytic inactivation of viruses using titanium dioxide nanoparticles and low-pressure UV light," J. Environmental Science and Health Part A, 2008, vol. 43, pp. 1261-1270.

J. Mo, et al., "Photocatalytic purification of volatile organic compounds in indoor air: A literature review," Atmospheric Environment, 2009, vol. 43, pp. 2229-2246.

E. Luevano-Hipolito, et al., "Synthesis, characterization and photocatalytic activity of $WO_3$/$TiO_2$ for NO removal under UV and visible light irradiation," Materials Chemistry and Physics, 2014, vol. 148, pp. 208-213.

S. Wang, et al., "Volatile organic compounds in indoor environment and photocatalytic oxidation: State of the art," Environment International, 2007, vol. 33, pp. 694-705.

USPTO: Office Action dated Oct. 27, 2022 in U.S. Appl. No. 17/007,341.

USPTO: Notice of Allowance dated Jan. 11, 2023 in U.S. Appl. No. 17/007,341.

* cited by examiner

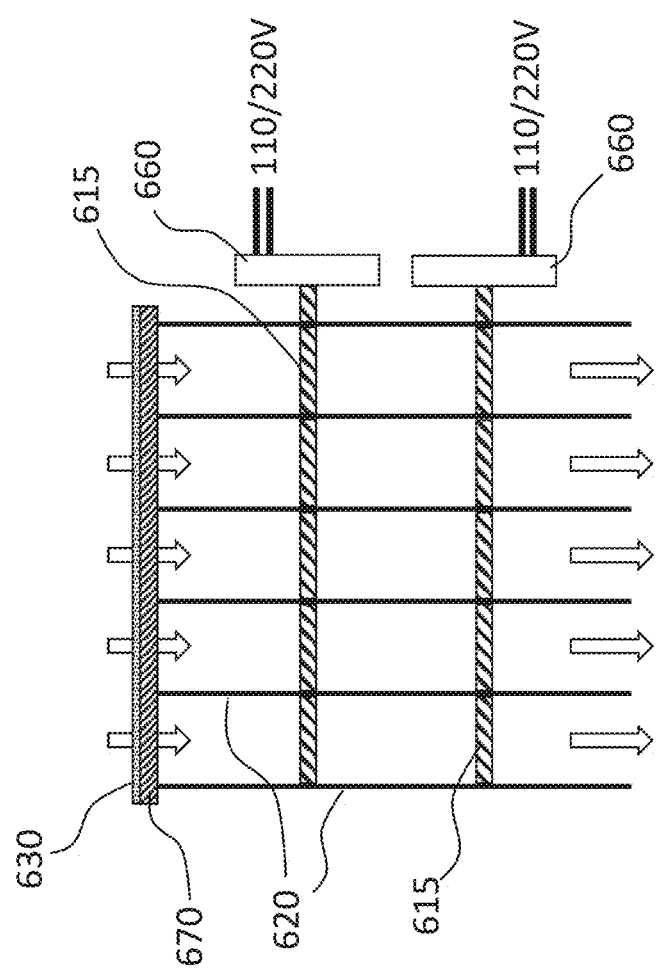

PHOTOACTIVATED SEMICONDUCTOR PHOTOCATALYTIC AIR PURIFICATION

CROSS-REFERENCE TO RELATED APPLICATIONS

This application is a continuation-in-part of U.S. patent application Ser. No. 17/007,341 filed Aug. 31, 2020 entitled "Photoactivated Semiconductor Photocatalytic Air Purification," the disclosure of which is incorporated herein by reference in its entirety for all purposes.

FIELD

The present disclosure generally relates to air purifiers and methods of air purification, and in particular to air purification comprising a photoactivated semiconductor photocatalytic system.

BACKGROUND

Air filtration commonly involves HEPA filters, activated carbon, ozonation and other oxidation processes including both ionization and photocatalysis. However, a majority of devices and methods in this field physically capture pollutants, as opposed to destroying them.

Most air purifiers and methods of air purification that involve a photocatalyst tend to employ $TiO_2$, including purifiers comprising $TiO_2$ coatings lining an enclosure radiated by UV-C light and $TiO_2$ catalytic membranes comprising HEPA filters infused with $TiO_2$. Photocatalytic coatings comprising $TiO_2$ have been marketed as having antimicrobial efficacy.

However, due to the inherent inefficiencies in air purification based on physical capture of contaminants, or $TiO_2$ photocatalytic oxidation thereof, new air purifiers and methods of air purification are still needed. More particularly, devices and methods are needed that actually destroy or deactivate airborne pollutants, especially airborne microbes like viral particles.

SUMMARY

It has now been discovered that by passing contaminated air over a photoactivated semiconductor photocatalytic system irradiated by incident radiation, the air can be cleaned and sanitized to a greater extent than by passing the contaminated air through filters or ionizers. It has also been discovered that air decontamination efficiency is even further enhanced by channeling contaminated air through stacked layers of photoactivated semiconductor with the layers arranged such that the air flows in a serpentine pattern across each layer in series through the stack.

It has further been discovered that air decontamination efficiency is greatly enhanced if each layer of photoactivated semiconductor in a stacked pattern is charged with a potential to create an electric field, and an ionizer is configured to charge contaminants present in the air so that the charged particles are attracted to each layer of photoactivated semiconductor.

In various embodiments, attraction of airborne particles, including microbes, to an internal geometry of a photocatalytic system is facilitated by both fluidic contacts and electromotive force and attraction.

It has further been discovered that air decontamination efficiency is greatly enhanced when the decontamination process employs a photoactivated semiconductor having a three-dimensional architecture, such as a photoactivated semiconductor having a 3-dimensionally ordered macroporous ("3-DOM") structure.

In various embodiments, a photoactivated semiconductor photocatalytic system herein comprises at least one semiconductor photocatalyst.

In various embodiments, a photoactivated semiconductor photocatalytic system herein comprises a single photocatalyst or a pair of photocatalysts, for example.

In various embodiments, a photoactivated semiconductor photocatalytic system herein comprises at least one semiconductor photocatalyst that is coupled to an electron transport layer (ETL) material, coupled to a hole transport layer (HTL) material, doped or surface modified, or any combination of the foregoing.

In various embodiments, a photoactivated semiconductor photocatalytic system herein is configured to produce e−/h+ pairs (i.e., electron/hole pairs) upon irradiation. Initial reductive e− capture by an acceptor "A" produces reductive species such as $.A^-$ radical anions, whereas initial oxidative h+ capture by a donor "D" produces oxidative species such as $.D+$ radical cations. The destruction of airborne pollutants, including microorganisms, is catalyzed either directly by the oxidizing power of the photogenerated holes (h+) or the reductive power of the photogenerated electrons (e−), or indirectly by reaction with radicals, anions, cations, $.A^-$ radical anions, and/or $.D+$ radical cations. Some of the reactive species that may be formed from oxygen or water in the presence of a photoactivated semiconductor photocatalyst include, but are not limited to, hydrogen peroxide ($H_2O_2$), hydroperoxyl radical ($HO_2.$), hydroxide anion ($HO^-$), hydroperoxyl radical anion ($HO_2.^-$), hydroxyl radical ($HO.$), hydronium ion ($H_3O+$) and/or superoxide radical anion ($.O_2^-$).

In general, a photoactivated semiconductor photocatalytic system herein is configured to produce reductive species and/or oxidative species in the presence of oxygen and/or water.

In various embodiments, air purifiers and methods of air purification include air sanitization through the destruction/deactivation of airborne microorganisms on the surfaces of a photoactivated semiconductor irradiated by incident radiation. In various embodiments, the air sanitization comprises a reduction in the number of airborne single-stranded RNA viral particles, including a reduction in the number of airborne SARS-CoV-2 viral particles characterized by deactivation of the viral particles on the surfaces of a photoactivated semiconductor irradiated by incident radiation.

In various embodiments, an air purifier comprises a photocatalytic system comprising at least one photoactivated semiconductor photocatalyst; and a lamp configured to irradiate the photoactivated semiconductor photocatalyst with incident radiation configured to excite the photoactivated semiconductor photocatalyst, wherein the photocatalyst system is configured to generate at least one reductive or oxidative reactive species in the presence of at least one of oxygen or water in contact with the photoactivated semiconductor photocatalyst.

In various embodiments, the at least one reductive or oxidative reactive species comprises at least one of hydrogen peroxide ($H_2O_2$), hydroperoxyl radical ($HO_2.$), hydroxide anion ($HO^-$), hydroperoxyl radical anion ($HO_2.^-$), hydroxyl radical ($HO.$), hydronium ion ($H_3O+$) and/or superoxide radical anion ($.O_2^-$).

In various embodiments, the at least one photoactivated semiconductor photocatalyst has an energy bandgap ($E_g$) of from about 12.4 eV to about 1.24 meV, referenced to NHE.

In various embodiments, the incident radiation has an energy ($E_s$), wherein $E_s \geq E_g$ of the at least one photoactivated semiconductor photocatalyst.

In various embodiments, the photocatalytic system comprises two photoactivated semiconductor photocatalyst having overlapping, non-overlapping, or offset bandgaps, wherein each bandgap is from about 12.4 eV to about 1.24 meV, referenced to NHE.

In various embodiments, the at least one photoactivated semiconductor photocatalyst is modified by at least one of coupling to an electron transport layer (ETL) material, coupling to a hole transport layer (HTL) material, doping, surface modification, or any combination thereof.

In various embodiments, the at least one photoactivated semiconductor photocatalyst comprises an elemental material, metal chalcogenide, metal oxide, metal oxyhalide, metal phosphate, metal hydroxide, metal nitride, metal molybdate, metal vanadate, or metal tungstate, wherein the metal is Ti, C, Cr, Mn, Fe, Co, Ni, Cu, Zn, Ga, Zr, Nb, Mo, Tc, Ru, Rh, Pd, Ag, Cd, In, Hf, Ta, W, Re, Os, Ir, Pt, Au, Hg or Tl.

In various embodiments, the at least one photoactivated semiconductor photocatalyst is selected from the group consisting of $Bi_2Mo_3O_{12}$, $Bi_2Mo_2O_9$, $Bi_2MoO_6$, $BiVO_4$, $Bi_2WO_6$, BiOBr, BiOI, $MoS_2$, CuO, $Cu_2O$, $MoO_3$, $WO_3$, $BiPO_4$, $Ag_3PO_4$, $TiO_2$, $SnO_2$, $InVO_4$, $FeVO_4$, $Ag_4V_2O_7$, $Fe_3O_4$, and mixtures thereof.

In various embodiments, the photocatalytic system comprises two photoactivated semiconductor photocatalysts consisting of $Bi_2MoO_6$ and $Ag_3PO_4$.

In various embodiments, the lamp comprises a low pressure mercury vapor lamp configured to radiate UV-C incident electromagnetic radiation at a wavelength of about 254 nm.

In various embodiments, the photocatalytic system further comprises a stack of PCB cards, each PCB card comprising a layer of the at least one photoactivated semiconductor photocatalyst disposed thereon, the photocatalytic system comprising a plurality of PCB cards stacked in a parallel and staggered arrangement creating a serpentine airflow pathway.

In various embodiments, the air purifier further comprises an ionizer configured to negatively or positively charge airborne contaminants in an air pathway leading into the photocatalytic system.

In various embodiments, the photocatalytic system comprises a photoactivated semiconductor photocatalyst having a 3-DOM structure.

In various embodiments, the 3-DOM structure comprises a 3-dimensional lattice resin having an open cell structure with holes of from about 1 mm to about 5 mm in average diameter, and wherein the at least one photoactivated semiconductor photocatalyst is present in the resin or on the resin.

In various embodiments, the 3-DOM structure comprises a 3D printed 3-dimensional lattice.

In various embodiments, the air purifier further comprises a humidifier configured to inject water vapor into an air pathway leading into the photocatalytic system.

In various embodiments, the air purifier further comprises an intake fan configured to pull contaminated air into the air purifier and move the air through the photocatalytic system.

In various embodiments, the air purifier further comprises an ozone trap configured to remove ozone generated from the photocatalytic system, the lamp or the combination thereof.

In various embodiments, a method of destroying or deactivating airborne contaminants present in contaminated air comprises contacting the contaminants present in the contaminated air with a surface of a photoactivated semiconductor photocatalyst irradiated with incident radiation configured to excite the photoactivated semiconductor, wherein irradiation of the photoactivated semiconductor photocatalyst generates reductive and/or oxidative reactive species from at least one of oxygen or water present on the surface of the photoactivated semiconductor photocatalyst and wherein the reductive and/or oxidative reactive species thus generated destroy or deactivate the airborne contaminants.

In various embodiments of the method, the reductive and/or oxidative reactive species generated comprise at least one of hydrogen peroxide ($H_2O_2$), hydroperoxyl radical ($HO_2\cdot$), hydroxide anion ($HO^-$), hydroperoxyl radical anion ($HO_2\cdot^-$), hydroxyl radical ($HO\cdot$), hydronium ion ($H_3O+$) or superoxide radical anion ($\cdot O_2^-$).

In various embodiments of the method, the at least one photoactivated semiconductor photocatalyst has an energy bandgap ($E_g$) of from about 12.4 eV to about 1.24 meV, referenced to NHE.

In various embodiments of the method, irradiation of the photoactivated semiconductor photocatalyst further comprises irradiation with incident radiation of having an energy ($E_s$) greater than or equal to a bandgap energy ($E_g$) of the at least one photoactivated semiconductor photocatalyst.

In various embodiments of the method, contacting the contaminants present in the contaminated air with a surface of a photoactivated semiconductor photocatalyst further comprises conveying the contaminated air through a serpentine airflow pathway configured between a plurality of spaced apart PCB cards stacked in a parallel arrangement, wherein each PCB card comprises a layer of the at least one photoactivated semiconductor photocatalyst.

In various embodiments, the method further comprises positively or negatively charging the contaminants in the contaminated air prior to the contaminants coming into contact with a surface of the photoactivated semiconductor photocatalyst.

In various embodiments, the method further comprises applying an electrical potential to each of the PCB cards such that an electric/electromagnetic field produced around each PCB card attracts charged contaminants to the layer of the at least one photoactivated semiconductor photocatalyst.

In various embodiments of the method, destroying or deactivating the contaminants further comprises destroying or deactivating an airborne microorganism.

In various embodiments of the method, destroying or deactivating the contaminants further comprises deactivating an airborne single-stranded RNA virus particle.

In various embodiments of the method, deactivating of the airborne single-stranded RNA virus particle further comprises contacting the airborne single-stranded RNA virus particle with a surface of the photoactivated semiconductor photocatalyst for a time sufficient for the reductive and/or oxidative reactive species thus generated to denature a biomolecule present in the single-stranded RNA virus particle.

In various embodiments of the method, the contaminants include airborne SARS-CoV-2 virus particles.

BRIEF DESCRIPTION OF THE DRAWING FIGURES

The subject matter is pointed out with particularity and claimed distinctly in the concluding portion of the specification. A more complete understanding, however, may best be obtained by referring to the detailed description and claims when considered in connection with the following drawing figures:

FIG. 6B illustrates a front plan view of the same functional design for use in an HVAC system.

DETAILED DESCRIPTION

Figure 1:
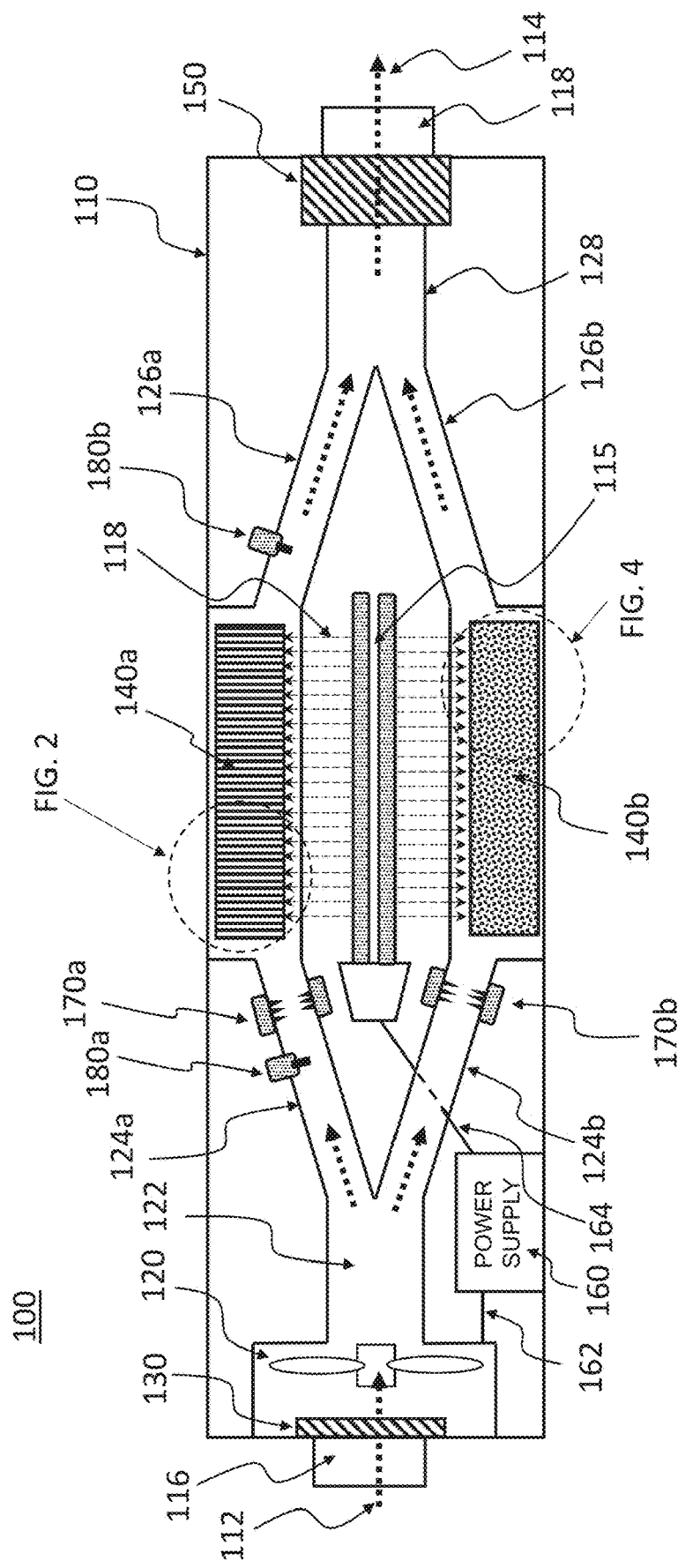
FIG. 1 illustrates an exemplary an air purifier, in accordance with various embodiments.

The detailed description of exemplary embodiments makes reference to the accompanying drawings, which show exemplary embodiments by way of illustration and their best mode. While these exemplary embodiments are described in sufficient detail to enable those skilled in the art to practice the invention, it should be understood that other embodiments may be realized and that logical, chemical, and mechanical changes may be made without departing from the spirit and scope of the inventions. Thus, the detailed description is presented for purposes of illustration only and not of limitation. For example, unless otherwise noted, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

In various embodiments, photoactivated semiconductor photocatalytic systems are described. In various embodiments, a photoactivated semiconductor photocatalytic system comprises at least one photoactivated semiconductor photocatalyst arranged in a 3-dimensional structure, such as, for example, a 3-dimensional structure comprising stacks of individual layers of catalyst, or comprising a lattice architecture.

In various embodiments, an air purifier and methods of air purification comprising a photoactivated semiconductor photocatalytic system are described.

In various embodiments, an air purifier and associated methods of air purification comprise a photoactivated semiconductor photocatalytic system further comprising at least one photoactivated semiconductor photocatalyst and an incident light source configured to irradiate and excite the photoactivated semiconductor photocatalyst present in the photocatalytic system.

In various embodiments, a photoactivated semiconductor photocatalyst herein is nanostructured. In various embodiments, a photoactivated semiconductor photocatalyst herein comprises nanoparticles. In various embodiments, a photoactivated semiconductor photocatalyst herein comprises a layer of nanoparticulate photocatalyst.

In various embodiments, a photoactivated semiconductor photocatalyst herein is configured to produce reductive species and/or oxidative species upon excitation by incident radiation when at least one photocatalyst in the photoactivated semiconductor photocatalyst is in the presence of oxygen and/or water.

In various embodiments, a photoactivated semiconductor photocatalytic system herein comprises at least one semiconductor photocatalyst.

In various embodiments, a photoactivated semiconductor photocatalytic system herein comprises a single photocatalyst or a pair of photocatalysts, for example.

In various embodiments, a photoactivated semiconductor photocatalytic system herein comprises at least one semiconductor photocatalyst that is coupled to an electron transport layer (ETL) material, coupled to a hole transport layer (HTL) material, doped or surface modified, or any combination of the foregoing.

In various embodiments, a photocatalytic system further comprises a stack of PCB (printed circuit board) cards, each PCB card comprising a layer of photoactivated semiconductor photocatalyst, wherein a plurality of PCB cards are stacked so as to create a series of air channels connected in a serpentine-like configuration such that air must flow across each photoactivated semiconductor photocatalyst layer present on each PCB card in the PCB card stack.

In various embodiments, a photoactivated semiconductor photocatalytic system further comprises a photoactivated semiconductor photocatalyst having a 3-dimensional structure.

In various embodiments, a photoactivated semiconductor photocatalytic system further comprises a photoactivated semiconductor photocatalyst having a 3-dimensionally ordered macroporous (3-DOM) structure.

In various embodiments, an air purifier and methods of air purification is capable of destroying/deactivating airborne pollutants, rather than simply physically trapping the pollutants. An air purifier and methods of air purification provide destruction/deactivation of airborne microbes, including the deactivation of viral particles. In various embodiments, an air purifier and methods of air purification provide deactivation of airborne single-stranded RNA virus particles, including deactivation of SARS-CoV-2.

Definitions and Interpretations

As used herein, the term "photoactivated semiconductor photocatalytic system" refers to a catalytic system comprising at least one semiconductor photocatalyst. In various embodiments, a photoactivated semiconductor photocatalytic system herein comprises a single photocatalyst or a pair of photocatalysts. In various embodiments, a photoactivated semiconductor photocatalytic system herein comprises at least one semiconductor photocatalyst that is doped, surface modified, coupled to an electron transport layer (ETL) material or coupled to a hole transport layer (HTL) material, or combinations thereof.

In various embodiments, the term "photoactivated semiconductor" refers generally to materials having an energy separation between their valance band (VB) and conductance band (CB), commonly known as a "bandgap." The bandgap of a photoactivated semiconductor may be energetically bridged using thermal, electromagnetic, or photo (i.e., light-based) energy. When activated by a sufficiently large energy source having energy ($E_s$) greater than or equal to the energy bandgap ($E_s \geq E_g$), electrons to migrate to the CB, leaving behind holes in the VB (i.e., forming e−/h+ pairs). After the creation of a e−/h+ pair, the electron can either drop back down from the conductance band filling the hole in the valance band in what is called recombination, or the holes and electrons can be separated so the holes and electrons may participate in oxidation and reduction reactions respectively. In various embodiments herein, a photocatalyst is a light activated semiconductor which is activated with the aim of facilitating reduction and/or oxidation reactions. The redox reactions serve the purpose of purifying air which may be achieved via direct photocatalyst/pollutant interaction or a pollutant's interaction with one of the photocatalyst's reactive products, byproducts or intermediate products, such as e.g., neutral radicals, anions, cations, radical anions, and/or radical cations, including, but not limited to, hydrogen peroxide ($H_2O_2$), hydroperoxyl radical ($HO_2\cdot$), hydroxide anion ($HO^-$), hydroperoxyl radical anion ($HO_2\cdot^-$), hydroxyl radical ($HO\cdot$), hydronium ion ($H_3O+$) and/or superoxide radical anion ($\cdot O_2^-$)). The composition of a semiconductor is a large chemical family containing single element specimens (e.g., Si), inorganic compounds (e.g., $TiO_2$), organic compounds (e.g., $C_{18}H_{12}$), and combination organic-inorganic compounds (e.g., $CH_3NH_3PbI_3$ also known as methylamino —$PbI_3$ or "$MAPbI_3$"). These substances may occur or be prepared in various physical forms including, but not limited to, crystalline, amorphous, polymeric, or combinations thereof.

Generally, semiconductor photocatalysts for use herein can be categorized by their chemical nature and/or their physical characteristics.

In various embodiments, a semiconductor for use herein is selected from the group of chemical substances consisting of single elemental materials, metal chalcogenides, metal oxides, metal oxyhalides, metal phosphates, metal hydroxides, metal nitrides, metal molybdates, metal vanadates, metal tungstates, and mixtures thereof, wherein the metal comprises any metal falling within the block of elements comprising Periods 4, 5 or 6 and Groups 4-13 elements of the Periodic Table of the Elements. The metals encompassed within this block of the Periodic Table are Ti, C, Cr, Mn, Fe, Co, Ni, Cu, Zn, Ga, Zr, Nb, Mo, Tc, Ru, Rh, Pd, Ag, Cd, In, Hf, Ta, W, Re, Os, Ir, Pt, Au, Hg and Tl. Exemplary semiconductor photocatalysts for use herein include, but are not limited to, $Bi_2Mo_3O_{12}$, $Bi_2Mo_2O_9$, $Bi_2MoO_6$, $BiVO_4$, $Bi_2WO_6$, BiOBr, BiOI, $MoS_2$, CuO, $Cu_2O$, $MoO_3$, $WO_3$, $BiPO_4$, $Ag_3PO_4$, $TiO_2$, $SnO_2$, $InVO_4$, $FeVO_4$, $Ag_4V_2O_7$, $Fe_3O_4$, and mixtures thereof.

In various embodiments, a semiconductor photocatalyst may be chemically modified. To increase the effectiveness of a photocatalytic semiconductor there are several methods of optimization: (1) the recombination rate of e−/h+ pairs can be lowered so there are more holes and electrons available to react; (2) reduction and oxidation reactions may be physically distanced to eliminate competitive redox reactions; (3) the bandgap may be tuned to utilize incident light more efficiently; (4) semiconductors may be placed in contact to create various junctions, or the surface may be modified to increase the adsorption, absorption, chemisorption or otherwise contact with pollutants to increase periodicity of reactions. These are the aims of the various types of modification. To achieve any one or combination of these modifications, a semiconductor photocatalyst herein may be modified by at least one of coupling to an electron transport layer (ETL) material, coupling to a hole transport layer (HTL) material, doping, surface modification, or any combination thereof.

In various embodiments, semiconductor photocatalysts for use herein may be modified or further optimized in methods which include, but are not limited to, metal and non-metal doping, surface alkalization, surface loading of metal and/or carbon, attachment to an electron transport layer (ETL), attachment to a hole transport layer (HTL), adjustment of particle size and/or geometry, or placing a semiconductor photocatalyst in contact with another semiconductor to form a junction (e.g., homojunction, heterojunction, etc.).

As used herein, the terms "electron transport layer" (ETL) and "hole transport layer" (HTL) refer to substances capable of reducing the recombination of e−/h+ pairs, e.g. altering the rate of recombination such that the substances undergoing redox reactions, namely oxygen and/or water, have certain time to react with the photogenerated electrons ($A \rightarrow A^-$) and photogenerated holes ($D \rightarrow D+$). In various embodiments, an ETL or HTL material for use herein is selected from the group consisting of single chemical elements such as metals, metal chalcogenides, metal oxides, metal oxyhalides, metal phosphates, metal hydroxides, metal nitrides, metal molybdates, metal vanadates, metal tungstates, and mixtures thereof, wherein the metal comprises any metal falling within the block of elements comprising Periods 4, 5 or 6 and Groups 4-13 elements of the Periodic Table of the Elements. The metals encompassed within this block of the Periodic Table are Ti, C, Cr, Mn, Fe, Co, Ni, Cu, Zn, Ga, Zr, Nb, Mo, Tc, Ru, Rh, Pd, Ag, Cd, In, Hf, Ta, W, Re, Os, Ir, Pt, Au, Hg and Tl. In various embodiments, an ETL or HTL material may also comprise a metal carbonate, or a composite of one of the above-mentioned chemical species and a metal carbonate, or graphene oxide, or an organic polymer, typically a fluorinated block or di-block electron conducting copolymer (e.g., a polythiophene). In various non-limiting embodiments, an ETL or HTL material for use herein is a metal oxide, or a composite of a metal oxide and a metal carbonate. In various embodiments, an ETL or HTL may comprise carbon, such as in the form of graphene, or a carbon nanotube (CNT, SWCNT, etc.). In various embodiments, an ETL or HTL material is selected from the group consisting of a metal M, ZnO, $TiO_2$, $SnO_2$, $Nb_2O_5$, $MoO_3$, $WO_3$, $V_2O_5$, NiO, $Cs_2CO_3$, graphene, graphene oxide, CNT, SWCNT, and combinations thereof.

The term "dopant" takes on its ordinary meaning in inorganic chemistry. A photoactivated semiconductor photocatalyst herein may be "doped." Dopants for use herein include, but are not limited to, Eu(III), F, Nd(III), Ag(I), Gd(III), Nb(V), Fe(III), Sm(III), Yb(III), Er(III), Cu(II), B, N, $PO_4^{3-}$, Co(II), Ni(II), and combination thereof. So, for example, a $BiVO_4$ photoactivated semiconductor photocatalyst for use herein may be doped with 0.01 wt. % Ag(I) powder. More extensive lists of dopants usable herein, including both organic and inorganic dopants, may be found in the semiconductor literature.

In various embodiments, a semiconductor photocatalyst for use herein in chosen on the basis of the photocatalyst exhibiting certain physical characteristics. For more than one semiconductor photocatalyst in a photoactivated semiconductor photocatalytic system, any two semiconductor photocatalysts may be chosen on the basis of various physical properties that they share, or that relate in some way.

In various embodiments, a semiconductor photocatalyst for use herein has a bandgap of from about 12.4 eV to about 1.24 meV. In embodiments where two semiconductor photocatalysts are present, their individual bandgaps may be overlapping, non-overlapping, or offset, as explained below.

When at least two semiconductor photocatalysts are present in a system herein, the bandgaps must be compared. A bandgap is the difference between the VBM valance band maximum and the CBM conductance band minimum. With these two energy levels dependent on electron shell structures and bond dynamics, it is possible to see a bandgap of the same size appearing at different locations; occurring when two substances have different VBM values but the same spacing between VBM and CBM. A bandgap overlap occurs when the bandgaps of two substances at least partially cover the same energies (e.g., substance 1 has a VBM of 1 eV and a bandgap of 2 eV and substance 2 has a VBM of 2 eV and a bandgap of 0.5 eV). Therefore, two substances with a 1 eV bandgap may have overlapping, non-overlapping (i.e., no junction), or offset bandgaps. If two substances have the same VBM and bandgap they create a homojunction. In most cases though there is an offset which characterizes a heterojunction. All junctions overlap, but not all overlaps are offset. The size and degree of offset further categorize heterojunctions. For example, two substances with the same bandgap and slightly different VBM form what is called a type-II hetero junction, while two substances with the same bandgap, but the VBM of one slightly below the CBM of the other, form a z-scheme heterojunction.

In various embodiments, semiconductor photocatalysts herein are capable of generating reductive and/or oxidative reactive species in the presence of oxygen and/or water. Semiconductor photocatalysts for use herein are chosen for their ability to generate at least one of hydrogen peroxide ($H_2O_2$), hydroperoxyl radical ($HO_2\cdot$), hydroxide anion ($HO^-$), hydroperoxyl radical anion ($HO_2\cdot^-$), hydroxyl radical ($HO\cdot$), hydronium ion ($H_3O+$) and/or superoxide radical anion ($\cdot O_2^-$) in the presence of at least one of oxygen or water.

In various embodiments herein, semiconductor photocatalysts are chosen in consideration of the incident radiation energy required for their excitation. As a general rule, the following approximations apply:

Infrared Range: 0.00124 meV-1.65 eV, or 1 nm to 750 nm;
Visible Range: 1.65 eV-3.1 eV, or 750 nm to 400 nm; and
Ultraviolet Range: 3.1 eV-12.4 eV, or 400 nm to 100 nm.

As used herein, the term "3-DOM" refers to "3-dimensionally ordered macroporous" structure, which is a type of three-dimensional architecture on a macroscopic scale. Self-assembling versions of 3-DOM structures are sometimes referred to as "inverse opal." Herein, a photoactivated semiconductor photocatalytic system may comprise a 3-DOM structure. In various embodiments, this three-dimensionally ordered porous material dictates the interaction of incident photos on the photocatalyst within the matrix, and creates certain airflow pathways and interactions between airborne pollutants and photocatalyst surfaces. In various embodiments, 3-DOM structure is used to create a three-dimensional macro-structured photocatalytic system from a photoactivated semiconductor photocatalyst. In various embodiments, a photocatalytic system comprises a 3-DOM photoactivated semiconductor photocatalyst.

In various embodiments, a 3-DOM structure can be made by 3D printing an inverse opal structure on a millimeter scale described using SLA or SLS 3D printing techniques with a photocatalytic resin (either infused or a type of sol-gel), or metal sintering material, respectively. 3-DOM materials include, but are not limited to, PFA*, FEP*, PTFE*, PVDF*, aluminum, HDPE, LDPE, fiberglass, quartz/fused quartz*, copper, and gold (*- indicates transparent materials). As discussed further below, a photoactivated semiconductor photocatalytic system having a 3-DOM structure may feature a photocatalytic resin lattice matrix, one or more photocatalysts embedded within a non-photoactive resin lattice matrix, one or more photocatalysts on or in the lattice, such as on the surfaces of the open cell structure, or any combination of the above. In instances where there are more than one photocatalysts present in a system, they can be distributed in any way in the 3-DOM structure (e.g., one catalyst is the resin, or one catalyst is in the resin and another on the lattice, and so forth).

As used herein, the terms "ultraviolet light" and "ultraviolet radiation" interchangeably refer to that portion of the electromagnetic spectrum from about 100 to about 400 nm in wavelength, corresponding to 12.4 eV to 3.1 eV. Although UV light may be used as the incident radiation for some of the types of photocatalysts chosen for use herein, any wavelength or range of wavelengths, including visible light, may be used in conjunction with the photocatalysts herein, depending on the nature of the photocatalyst. In various embodiments, an incident wavelength may be chosen for its dual function, namely, to activate a particular semiconductor photocatalyst and inactivate microorganisms. An example is UV-C incident light at about 250 nm, known to activate certain photocatalytic systems and denature microorganisms such as SARS-CoV-2 virus.

As used herein, the term "lamp" is used broadly to include any light energy source, regardless of whether the source resembles a traditional incandescent bulb or not. Non-limiting examples of lamps include mercury vapor lamps, halogen lights, light-emitting diodes (LEDs, including UV LEDs and plasma UV emitters), gas discharge lamps, electrical arcs, black lights, fluorescent lamps, incandescent lamps, lasers, and plasma and synchrotron sources.

As used herein, the term "single-stranded RNA virus" takes on its ordinary meaning in virology to include both positive-sense RNA viruses (Group IV) and negative-sense RNA viruses (Group V). The Group IV viruses include such well-known pathogens as hepatitis C, West Nile, dengue, MERS, and SARS, including SARS-CoV-2. The Group V viruses also include well-known pathogens, the most infamous perhaps being Ebola. For simplicity, the terms "Groups IV/V viruses" or "ssRNA viruses" may be used interchangeably with one another and interchangeably with the term fully written out terms "positive-sense single-stranded RNA viruses" and "negative-sense single-stranded viruses."

As used herein, the terms "air sanitization," "sanitizing air," and "sanitized air," are interchangeably used to indicate at least some level of microbe kill (i.e., a measurable reduction in the number of airborne microorganisms) by an air purifier or methods of air purification according to the present disclosure. For example, air that is sanitized may indicate a sanitizing level (3-log, or 99.9%) reduction in at least one organism. Microbes, or microorganisms adversely effected by an air purifier or methods of air purification disclosed herein, may include any species of bacteria, virus, mold, yeast, or spore. Thus, air sanitization encompasses reduction of airborne bacteria, viruses, molds, yeasts, or spores. In various embodiments herein, an air purifier or methods of air purification herein, reduce the number of airborne viral particles, including single-stranded RNA viruses such as SArS-CoV-2.

In various embodiments, airborne microorganisms coming into contact with a photoactivated semiconductor photocatalyst system herein, appropriately irradiated with incident energy light, experience cell death, destruction, and/or inactivation. The sanitizing effect made possible by the photocatalyst system is not limited by a particular mechanism of action, although it remains possible that reductive and/or oxidative reactive species generated from oxygen and/or water present on the photocatalyst are involved. For example, an air sanitizing effect measured for a photocatalyst system may be the result of intracellular mutations, inhibition of certain cellular processes, rupture of a cell wall, or a nondescript inactivation of the organism, such as in the case of viruses that may be deactivated simply by free-radical breakdown of biomacromolecules such as RNA present in the viruses. An example of inactivation of the SARS-CoV virus on a titanium photocatalyst has been described in Wei Han, et al., "The inactivation effect of photocatalytic titanium apatite filter on SARS virus," *Progress in Biochemistry and Biophysics*, 31(11), 2004.

I. Air Purifier—General Aspects

In various embodiments, an air purifier is described. The air purifier is capable of destroying/deactivating airborne pollutants, including the ability to reduce the number of viable airborne microbes in contaminated air, including bacteria, viruses, molds, yeasts and spores. A measurable reduction in the number of airborne microbes is associated with deactivation of the organisms rather than physical entrapment where the microbes might still be viable even though they are physically immobilized. Here, reductive and/or oxidative reactive species produced from the photoactivated semiconductor photocatalytic system upon excitation, deactivate microorganisms in contact with the surfaces of the photoactivated semiconductor photocatalyst, such as through denaturing of biomolecules essential to the organism.

In various embodiments, an air purifier comprises a photocatalytic system and an incident light source configured for the photocatalytic system. The photocatalytic system further comprises a photoactivated semiconductor. The incident light source is configured and is appropriately positioned so as to excite the photoactivated semiconductor within the photocatalytic system. In various embodiments, the photocatalyst system is configured to generate reductive and/or oxidative reactive species from oxygen or water. In various embodiments, the photocatalytic system is configured to generate at least one of hydrogen peroxide ($H_2O_2$), hydroperoxyl radical ($HO_2\cdot$), hydroxide anion ($HO^-$), hydroperoxyl radical anion ($HO_2\cdot^-$), hydroxyl radical ($HO\cdot$), hydronium ion ($H_3O+$) and/or superoxide radical anion ($\cdot O_2^-$) by the choice of the photoactivated semiconductor photocatalyst and the presence of at least one of oxygen or water.

In various embodiments, a photoactivated semiconductor photocatalyst is disposed as a layer on a printed circuit board (PCB) referred to herein as a "PCB card." In various embodiments, a photoactivated semiconductor photocatalyst is adsorbed onto the card and cured thereon to produce the PCB card comprising the photoactivated semiconductor photocatalyst. In various embodiments, the adhesive may be applied to a PCB card by dipping, brushing, rolling, spraying, amongst other methods. Particles of semiconductor photocatalyst may then be adhered to the surface of the PCB card via the adhesive present. In various embodiments, the photocatalyst may be premixed with an adhesive and the mixture applied to the PCB card by any of the aforementioned methods.

In various embodiments, a photocatalyst is dispersed on an adhesive coated PCB card by dusting, fogging, sprinkling, sieving, dipping, dabbing, etc. After the photocatalyst is dispersed, the adhesive can be cured according to the nature of the adhesive used. The specific combination of application methods depend on geometry of the PCB card and the overall photocatalytic system. In other variations, particles of photocatalyst may be hot-pressed into an appropriate surface. This can be done by heating for example PVDF and pressing it into a glass plate with photocatalyst particles dusted onto its surface and then repeating the process for both sides. As an alternate, a photocatalyst may be synthesized directly on the surface of a photocatalytic system or an element therein using normal methods such as vapor deposition, spin-coating, sol-gel, epitaxy molecular beams, etc. These syntheses tend to be more demanding and expensive but have greater rigor and control.

In various embodiments, a stack of these coated PCB cards are appropriately arranged to destroy/deactivate airborne pollutants conveyed past the photoactivated semiconductor photocatalyst layers on the PCB cards. In various embodiments, an electrical potential is applied across each PCB card such that the photoactivated semiconductor photocatalyst present on the PCB card is, in effect, polarized. The applied potential to the PCB card results in an electric/ electromagnetic field around the PCB card. In various embodiments, an ionizer is provided upstream from the stack of PCB cards to electrically charge pollutants present in the contaminated air so that the charged particles collect on the photoactivated semiconductor photocatalyst layers by electromotive forces. In various embodiments, the polarized PCB cards replace the collector plates in a conventional ionizer. In all likelihood, the photocatalytic layer itself is not polarized per se, but rather the underlying electrodes are polarized by the applied potential such that charged pollutant particles run into the photocatalyst layer that blocks the route of the charged particles to the polarized electrodes underneath the photocatalyst layer.

In various embodiments, the photocatalytic system further comprises a photoactivated semiconductor photocatalyst coated onto and into a three-dimensional lattice, such as a 3-DOM structure. In various embodiments, the photoactivated semiconductor photocatalyst is the lattice, or is within the lattice.

In various embodiments, and in addition to at least one photocatalytic system and associated incident radiation source, an air purifier herein may further comprise any one or combination of an exterior housing, an air intake port, a prefilter, an intake fan to push air through, an ionizer, air splitters, air collimators, and capillary channels as needed, air ducting, an ozone trap, an outlet fan to pull air through, an outlet port, a power supply, an external power supply cord, various indicator lights, circuit boards, computer processors and controllers, sensors, internal wiring, bus bars, transformers, rectifiers, alarms, and remote controls as needed. Some of these general aspects will be appreciated in reference to the various drawing figures.

With reference now to FIG. 1, an air purifier 100 in accordance with various embodiments comprises at least one photocatalytic system (two are shown, 140*a*/140*b*, which may be the same or different) and at least one lamp 115 physically configured and appropriately positioned to irradiate the photocatalytic system 140 with incident radiation 118. In FIG. 1, the bolded and dashed directional arrows such as 112 and 114 indicate directional air flows. The lighter dashed directional arrows 118 indicate electromagnetic radiation, such as IR, UV or visible light, emanating from the lamp 115. The left side of the air purifier 100 as illustrated is the intake side for entry of contaminated air to be purified, whereas the right side of the air purifier 100 as illustrated is the outlet side for exit of the purified air.

In FIG. 1, two separate photocatalytic systems 140a and 140b are configured on opposite sides of the lamp 115, although this particular configuration is not meant to be limiting. Any number of photocatalytic systems can be employed in the air purifier 100. For example, a plurality of photocatalytic systems (140a, 140b, 140c, and so forth) can be configured around the lamp 115 with the lamp 115 centrally positioned to irradiate the multiple photocatalytic systems positioned radially around the lamp 115. In other embodiments, more than one lamp 115 (115a, 115b, 115c, and so forth) may be utilized to irradiate multiple photocatalytic systems, and the various lamps may be physically configured to irradiate the same, different or overlapping wavelengths as needed. For example, one lamp may irradiate UV-C light at 254 nm to excite a particular photocatalytic system, whereas another lamp present in the air purifier 100 may irradiate light in the visible spectrum to excite another photocatalytic system. In various embodiments, a plurality of LEDs may be configured around or within a photocatalytic system. In various embodiments, the photocatalytic systems may be different, (e.g., photocatalytic systems 140a and 140b), in that each may have a unique photoactivated semiconductor photocatalyst configuration, or a unique physical structure, requiring its own dedicated lamp 115 capable of irradiating a particular wavelength of incident radiation appropriate for that particular photocatalytic system. For example, one photocatalytic system 140a may require UV-C (254 nm) incident radiation to excite the photoactivated semiconductor photocatalyst therein, whereas another photocatalytic system 140b may require visible light to excite the photoactivated semiconductor photocatalyst therein. In various embodiments, optical fibers may be used to convey light through convoluted pathways and into narrow interstices present in the photocatalytic system that might otherwise not receive incident radiation from the lamp 115.

As will be described in more detail herein, each photocatalytic system 140a/140b comprises a photoactivated semiconductor photocatalyst configured in a three-dimensional architecture. In various embodiments, the photocatalytic system may comprise a three-dimensional array of stacked PCB cards, wherein each PCB card comprises a layer of the photoactivated semiconductor photocatalyst. In other embodiments, the photocatalytic system may comprise a three-dimensional lattice, such as a 3-DOM structure, having the photoactivated semiconductor photocatalyst on and/or in the lattice, or where the lattice matrix material is a photocatalyst. In various embodiments, the photocatalytic system comprises a 3-DOM photoactivated semiconductor photocatalyst.

In various embodiments, the lamp 115 provides incident radiation of energy ($E_s$) greater than or equal to the energy bandgap ($E_g$) of each of the photoactivated semiconductor components that may be present within the photocatalytic system. That is, the lamp is configured such that $E_s \geq E_g$ for at least one photocatalyst in the system. In various embodiments, the lamp 115 comprises a lamp that provides infrared light. In various embodiments, the lamp 115 comprises a lamp that provides visible light. In various embodiments, the lamp 115 comprises a UV lamp. In various embodiments, the lamp 115 comprises a UV-C lamp providing incident UV radiation 118 at from about 200 nm to about 280 nm. In various embodiments, the UV-C lamp is configured to provide incident radiation 118 having a wavelength of about 254 nm. In certain embodiments, the lamp 115 comprises a mercury low pressure UV lamp, further comprising a quartz tube, an electrode, mercury and an inert gas. An exemplary low pressure lamp emitting almost entirely 254 nm radiation is available, for example, from Helios Quartz America, Inc, Sylvania, Ohio.

In various embodiments, the air purifier 100 may further comprise a housing 110 with panels defining an exterior surface and an interior space. The housing may be constructed of conventional materials, such as plastic or metal, and may appear simply as a galvanized sheet metal box. The housing 110 may be designed for aesthetics if the air purifier 100 will be visible to the user, such as if configured as a portable appliance, or the housing 110 might be entirely utilitarian where the outward appearance may not be that important, such as if the air purifier 100 is configured for retrofitting into an existing HVAC system. The housing may have any shape or size, and may be rectangular in cross-section as illustrated in FIG. 1. The housing 110 may include any number of vents and cooling fans to move heat from the interior of the air purifier (e.g., heat generated from the lamps), any number of hinging, sliding or otherwise removable access doors or panels, indicator lights such as LEDs, switches, buttons, piezo beepers/buzzers, Bluetooth transmitter, water inlet/outlet fittings, and electrical cords. Any one or combination of these elements may be physically mounted on or through the housing 110 and may be configured to be purposely visible on or audible from the exterior surface of the housing 110. These features are not illustrated in FIG. 1 for the sake of clarity.

In various embodiments, the air purifier 110 may include any number and type of sensors (e.g., 180a, 180b, etc.), along with a microprocessor to adjust and/or maintain heating, cooling, pressure, humidity, airflow, etc., based on the data collected for these variables. In various embodiments, the air purifier 110 may further comprise at least one sensor 180a/180b selected from chemical sensors (VOCs, ozone, etc.), temperature sensors, pressure sensors, humidity/moisture sensors, and airflow/air speed sensors.

In various embodiments, the one or more sensors 180a/180b may be placed both before and after a photocatalytic system (140a/140b), respectively, to measure variables such as total VOCs (TVOCs), pressure, temperature, air speed, humidity, ozone content, etc., on both sides of a photocatalytic system. These two data points, a data point obtained from sensor 180a configured in an inlet to the photocatalytic system 140a, and a data point obtained from sensor 180b configured in an outlet from the photocatalytic system 140a, may then be relayed to a microcontroller/microprocessor configured to perform operations such as increasing/decreasing lamp power (incident radiation intensity), air humidifying, fan speeds, and the like, with the goal of maintaining high efficiency VOC-input VOC-output ratio, indicative of clean air. This gives the purifier a way to ensure a predetermined single pass air scrub level utilizing real-time internal data, and serves to conserve energy in cleaned spaces by dropping system power demands when pollutant levels are measurably low. The microcontroller may be external to the air purifier 110, and may comprise a laptop computer or other device. The sensors 180a/180b may communicate wirelessly to a computer.

With continued reference to FIG. 1, the air purifier 110 further includes air ductwork. This ductwork may be as simple as necessary to convey contaminated intake air through the one or more photocatalytic systems and back out to an environment outside of the air purifier 100. The ductwork internal to the air purifier 100 may also be as complicated as needed to convey air into and through a multiplicity of photocatalytic systems, each one possibly comprising its own air flow labyrinth, and through any number of other elements in the device such as filters, ionizers, and sensors. So, for example, intake air 112 may come into an intake tube 122 that splits into similar or identical air channels 124a and 124b. In this example, there are two air channels 124a and 124b in order to coincide with use of two photocatalytic systems 140a and 140b. As mentioned above, an air purifier 100 may comprise a plurality of individual photocatalytic systems, and thus the air ductwork may be much more complicated than illustrated in FIG. 1. Air may need to be split into a plurality of air channels (124a, 124b, and so forth) so as to feed contaminated intake air into each one of a plurality of photocatalytic systems (140a, 140b, and so forth). As further illustrated in FIG. 1, air that has been purified by the photocatalytic systems 140a/140b is then conveyed through outlet air channels 126a and 126b and into an outlet tube 128. As mentioned, when more than two photocatalytic systems are employed, the number of outlet air channels (126a, 126b, and so forth) can match the number of intake air channels (124a, 124b, and so forth), and match the number of photocatalytic systems employed (140a, 140b, and so forth). Purified air 114 then exits the air purifier 100 through the outlet port 118. Features at the intake side and the outlet side of the air purifier 100 are discussed in more detail herein. Although the air purifier is illustrated in FIG. 1 with only one intake fan 120, any number of fans may be employed in the air ductwork. In other words, a single fan 120 at the intake end of the device may be insufficient to push air through and out of the air purifier 100. Additional fans may be configured within air channels on either or both the intake and outlet side of the device. Further, an outlet fan may be employed to pull air 114 out of the air purifier. All of the fans may be controlled by a computer processor, each one being adjusted so that the air flow through the entire air purifier 100, and the purification of contaminated air, are optimized.

In various embodiments, the air purifier 100 comprises at least one ionizer 170a/170b configured in the air ductwork on the inlet side of the air purifier 100. In the embodiments illustrated, a first ionizer 170a is configured in the intake air channel 124a and a second ionizer 170b is configured in the intake air channel 124b. Each of the one or more ionizers are configured to provide a charge on various airborne pollutants present in the contaminated air prior to entry of the contaminated air into the one or more photocatalytic systems 140a/140b. As explained in more detail herein, various elements of a photocatalytic system herein can act as the collection plates in a conventional ionizer, such that the charged pollutant particles entering the photocatalytic system 140a/140b are attracted to various charged features within the photocatalytic system 140a/140b, such as layers of photoactivated semiconductor photocatalyst. In various embodiments, the at least one ionizer 170a/170b is configured to positively charge pollutant particles or negatively charge pollutant particles. In various embodiments, the at least one ionizer 170a/170b is configured to positively or negatively charge airborne microorganisms, such as virus particles, before the microorganisms enter the one or more photocatalytic systems 140a/140b where they are attracted to layers of photoactivated semiconductor photocatalyst having a charge.

In various embodiments, the ionizer 170a/170b may comprise an electrostatic discharge ionizer (ESD) configured to provide corona ionization into the contaminated air passing therethrough. In various embodiments, the ionizer may comprise ESD needles protruding into the airduct, as illustrated in FIG. 1. In various embodiments, an electrical current creates bipolar ionized air. The ionizer applies a high-voltage electrical current composed of a flow of electrons to the protruding needles. Electrostatic repulsion causes the electrons to detach from the needles where they attach themselves to the pollutants in the contaminated air, forming negative ions, which are attracted to the various electrically charged elements within the photocatalytic systems 140a/140b. Corona ionization may comprise AC and DC ionization. AC ionization uses one emitter to produce both positive and negative ions, whereas DC ionization uses separate positive and negative emitters running simultaneously to create bipolar ions. In various embodiments, the negative pole of the ionizer may be connected to the ESD needles and the positive pole of the ionizer connected to a feature within the photocatalytic system. In other embodiments, the ionizer ESD needles provide bipolar ions that attach to various features in the photocatalytic system that are similarly bipolarized with both (+) and (−) poles.

In various embodiments, the air purifier 100 comprises at least one power supply 160 and its associated components such as step-down transformers, AC-DC rectifiers, wiring and connectors. The power supply 160 may be wired at least to the intake fan 120 via the wiring 162, to the lamp 115 via the wiring 164, and to the ionizers 170a/170b (wiring not shown) so that the required electrical power (voltage, phase, current) is supplied to these and other electrical components present, such as additional fans, sensors, and so forth. More than one power supply 160 can be employed, such as having a high voltage/amperage power supply for the one or more lamps, and a low voltage/amperage power supply for such components as fans and circuit boards, or such that AC is supplied to one component and DC to another. One or more external electrical supply cords can be wired to the power supply, such as through a grommet configured in the air purifier housing 110, with the end of the cord having the appropriate configuration for 110V or 220V and ground, or the necessary pins for electrical outlets found in other countries besides the U.S.

In various embodiments, the air purifier 100 may further comprise a prefilter 130 as illustrated in FIG. 1. A prefilter for use herein may be configured on either side of the intake fan 120 so long as the prefilter 130 is positioned before the photocatalytic systems 140a/140b. The purpose of the prefilter 130 is to remove large particulates, particularly inanimate materials, from the intake air that would otherwise accumulate on the photocatalytic system and eventually block the photocatalytic surfaces.

In various embodiments, the prefilter 130 comprises a HEPA filter, which may be any grade of air filter. HEPA filters are generally categorized by MERV ratings (Minimum Efficiency Reporting Value) ranging from 1 to 20. For use herein, the prefilter 130 may comprise a filter having a MERV rating of up to about 12. Filters with MERV ratings from about 14-16 are capable of trapping airborne bacteria, and filters with MERV ratings from about 17 up to 20 are capable of trapping airborne viruses. Filtration at these levels is not necessary since it is the photocatalytic systems in the air purifier 100 that will destroy the airborne bacteria, viruses, molds, yeasts and spores. The prefilter 130 may be chosen for its ability to filter out the larger inanimate particles coming into the air purifier 100 such that the photocatalytic systems 140a/140b are not soiled and rendered ineffective by a buildup of these soils. For example, the prefilter 130 may comprise a home or institutional air filter having a MERV rating of from 1 to about 12, and more preferably from about 5 to about 12. The prefilter 130 may comprise a cheap disposable filter, a better quality home box filter, or a superior quality commercial HVAC filter. The prefilter 130 may be appropriately sized to cover the intake port 116, and may be fit inside the intake port 116. In various embodiments, the intake port 116 and the prefilter 130 form an assembly configured to be removable from the housing 110 so that the prefilter 130 can be easily replaced when needed. A prefilter for use herein may be manufactured out of a variety of materials, e.g., paper, pulp, cloth, cotton, nonwoven polymer fibers, polymeric foam, fiberglass, metal mesh, etc., or any combinations of these materials of construction.

With continued reference to FIG. 1, the air purifier 100 may comprise an ozone trap 150 configured on the outlet end of the air purifier 100. For example, the ozone trap may be inline within the outlet tube 128, or just before or after the outlet tube 128. In various configurations, the ozone trap 150 may be positioned at the end of the outlet side of the air purifier, such as between the outlet tube 128 and the outlet port 118. In this way, the purified air 114 exiting from the outlet port 118 of the air purifier 100 is stripped of any ozone that may have formed from oxidative processes in the photocatalytic systems 140a/140b and from the lamp 115 or from any ionizer that may be present.

In various embodiments, the ozone trap 150 may be any sort of filter or support impregnated with one or more substances, like activated carbon, permanganate, perlite or other ozone destroyer. In various embodiments, the ozone trap 150 comprises a manganese dioxide/copper oxide catalyst. This ozone trapping catalyst is available under the brand name Carulite® 200, from Carus Corporation, LaSalle, Ill.

Photocatalytic Systems

As discussed herein, an air purifier and methods of air purification in accordance with the present disclosure comprise at least one photocatalytic system 140a/140b, such as shown in FIG. 1 (illustrated with two photocatalytic systems 140a and 140b that may be the same or different). In various embodiments, a photocatalytic system for use herein comprises at least one photoactivated semiconductor photocatalyst.

In various embodiments, the photocatalytic system comprises photoactivated semiconductor photocatalyst nanoparticles. In instances where the photoactivated semiconductor photocatalyst comprises more than one substance (e.g., a pair of photocatalysts, or a semiconductor photocatalyst coupled to an ETL or HTL material), each component may be intermixed within a single nanoparticle, e.g., with a core/shell structure, or each component may consist of its own nanoparticles and these nanoparticles of different composition are intimately mixed. In various embodiments, photoactivated semiconductor substances are crystalline or amorphous and not comprising identifiable nanoparticles.

In various embodiments, the photocatalytic system comprises a three-dimensional structure. A three-dimensional overall structure of a photocatalytic system may be the result of coating a photoactivated semiconductor photocatalyst onto and into a macroscopically sized three-dimensional lattice, such a 3-DOM structure, or may be the result of stacking coated PCBs into a 3-dimensional array, wherein each PCB card comprises a layer of a photoactivated semiconductor photocatalyst. In either of these two non-limiting embodiments, a three-dimensional configuration (3-DOM structure or stacked coated PCB cards) provides unique airflow passageways for a photocatalytic system, thus increasing the likelihood that airborne pollutants will interact with the photoactivated semiconductor photocatalyst. These and other embodiments are discussed in more detail herein.

In various embodiments, a photoactivated semiconductor photocatalyst for use in the photocatalytic systems herein comprises at least one semiconductor photocatalyst as defined herein above. In various embodiments, two photoactivated semiconductor photocatalysts for use in the photocatalytic systems herein are independently selected from the group consisting of $Bi_2Mo_3O_{12}$, $Bi_2Mo_2O_9$, $Bi_2MoO_6$, $BiVO_4$, $Bi_2WO_6$, $BiOBr$, $BiOI$, $MoS_2$, $CuO$, $Cu_2O$, $MoO_3$, $WO_3$, $BiPO_4$, $Ag_3PO_4$, $TiO_2$, $SnO_2$, $InVO_4$, $FeVO_4$, $Ag_4V_2O_7$, $Fe_3O_4$, and mixtures thereof.

In various embodiments, a photoactivated semiconductor photocatalytic system comprises at least two semiconductor photocatalysts. In various embodiments, a photoactivated semiconductor photocatalytic system comprises a mixture of $Bi_2MoO_6$ and $Ag_3PO_4$. In various embodiments, a photoactivated semiconductor photocatalytic system comprises a mixture of $Bi_2MoO_6$ and $Ag_3PO_4$ in a (w/w) ratio of from about 1:5 to about 1:15. In various embodiments, a photoactivated semiconductor photocatalytic system comprises a mixture of $Bi_2MoO_6$ and $Ag_3PO_4$ in a (w/w) ratio of about 1:9.

Formation of reductive and/or oxidative reactive species as discussed herein above requires oxygen or water molecules on the photoactivated semiconductor photocatalyst. Oxygen will always be present in the contaminated air entering the air purifiers disclosed herein for purification.

For the air purifier and methods of air purification herein, it may suffice that the contaminated air for purification is moist. That is, the contaminated air to be cleaned may have a certain relative humidity such that sufficient water is present on the surfaces of the photoactivated semiconductor photocatalyst (e.g., condensed on the photocatalyst). In some instances, the water from humid air condensed on the photoactivated semiconductor photocatalyst and may or may not be visible to the naked eye, but is present in sufficient quantity to form reductive and/or oxidative reactive species.

For purification of dry contaminated air, where there is insufficient humidity in the contaminated air to provide water to the photocatalytic systems 140a/140b, water or humidity may be brought into the air purifier. As mentioned, humidity sensors within the air purifier can collect humidity data, send the data to a microprocessor, and the microprocessor may control a secondary device to add moisture to the inlet air or to the photocatalytic system. For example, air purifier 100 in FIG. 1 may further comprise a water or water vapor inlet, and where necessary, a water or water vapor outlet (these optional features are not illustrated). The water inlet to the air purifier 100 may be configured to feed water to a built-in humidifier configured inside the air purifier 100. In various embodiments, water vapor from the built-in humidifier may be injected directly into the air stream flowing through the air inlet tube 122, wherein the moisture is then carried along with the contaminated air to the photocatalytic systems 140a and 140b. The temperature of the catalyst surfaces within the photocatalytic systems 140a and 140b may also be lowered to temperatures below the dew point of the intake air, promoting water condensation on the catalyst surfaces. In other embodiments, water may be atomized into the air intake tube 122 through an atomizing nozzle under pressure or by way of an ultrasonic nebulizer, and these fine particulates are carried to the photocatalytic surfaces by the movement of the air.

1. PCB Card Stack Photocatalytic System

In various embodiments, an air purifier and methods of air purification comprise at least one photocatalytic system (FIG. 1, 140*a*/140*b*) that further comprises a PCB card stack. A PCB card stack refers herein to a plurality of printed circuit boards (PCBs) configured in a three-dimensional array, wherein each PCB is coated with a photoactivated semiconductor photocatalyst. In various embodiments, the stacking of spaced apart and parallel arranged PCB cards (i.e., face to face) creates a particular airflow pathway through the photocatalytic system, such as a serpentine pathway.

Various embodiments of a PCB card stack 200 is illustrated in FIG. 2, noting that in FIG. 1, a dashed circle indicates that FIG. 2 is an enlarged view of one of the photocatalytic systems 140*a* that features the stacked PCB card configuration.

In FIG. 2, a PCB card stack is shown fashioned as a photoreactor contained in a housing 210. The housing 210 may be nothing more than an open frame so that the light emitted from the incident radiation source (lamp) can still impinge on the photocatalysts present as layers in the photocatalytic system 200 without the structure blocking the light. In other embodiments, the housing 210 can be quartz glass or other suitable structure transparent to the incident radiation. The housing 210 is also used to ensure air flows properly through the photocatalytic system 200 so as to make contact with layers of photoactivated semiconductor photocatalyst.

As illustrated in FIG. 2, the PCB card stack photocatalytic system 200 further comprises an air inlet 202 through which contaminated air 203 enters, and an air outlet 204 out which purified air 205 exits. With reference to FIG. 1, the air channels 124*a*/124*b* can be directed into the air inlet 202 of PCB card stack 200, and the air outlet channels 126*a*/126*b* can be connected to the air outlet 204 of PCB card stack 200. As discussed previously, the number of air channels may depend on the number of photocatalytic systems 200 employed in the air purifier.

The contaminated air 203 entering the photocatalytic system 200 comprises one or more airborne contaminants 206, such as one or more species of airborne microorganism.

As illustrated in FIG. 2, the PCB card stack photocatalytic system 200 comprises a plurality of coated PCB cards 220, spaced apart to provide a series of air channels 221. Although in FIG. 2 only ten PCB cards 220 are shown in the PCB card stack photocatalytic system 200, the illustrated example should not be interpreted as being limited. The number of PCB cards in a PCB card stack may be quite large, such as dozens up to hundreds of PCB cards or more. As shown, the individual PCB cards are spaced apart and stacked in a parallel configuration, but in a slightly staggered arrangement so that air flow (indicated by the dashed directional arrows) follows a serpentine pathway through the system 200, necessarily passing across each coated PCB card as the air is conveyed through each channel 221 configured between the cards in the array. Stated another way, the serpentine airpath ensures the contaminated air passes over each PCB card in series through the stack.

With continued reference to FIG. 2, each coated PCB card 220 further comprises an electrical connector 230, each connector further comprising an electronic interface 231 connecting to electronic components on the PCB card, along with (+) and (−) leads. This illustration should by no means be interpreted as limiting. For example, the (+) and (−) electrodes may be on opposing edges of a PCB card rather than together on the same edge. In other embodiments, each card only receives a (+) or a (−) pole, and the opposite polarity connection might be to an element configured outside of the photocatalytic system 200. Or, cards might alternate as positively charged or negatively charged. In the illustration, each PCB card is polarized by applying a (+/−) potential on each card such that each card is bipolar.

In various embodiments, each of the (+) leads from all the PCB cards are ganged together and each of the (−) leads from all the PCB cards are ganged together. In various embodiments, each card is plugged into an electrified frame such that plugging the cards into the frame acts to gang each of the (+) and each of the (−) leads together, making the system more modular.

The electrical connectors 230 allow a potential to be applied to each PCB card so as to polarize each PCB card, i.e., make the card bipolar, which is explained below in reference to FIG. 3. In various embodiments, PCB cards 220 can be pulled out from the housing 210 to be cleaned, recoated with photocatalyst, or replaced, as necessary.

In various embodiments, the air flow through the PCB card stack photocatalytic system 200 depends on a number of variables, including the input air pressure (controlled to some extent by the intake fan 120 in FIG. 1 to push air through, and an optional output fan, not shown, to pull air through), the number of PCB cards 220 in the stack dictating the number of air channels 221, and the size of the individual air channels 221, which is determined in part by the spacing between PCB cards 220.

In various embodiments, a photocatalytic system comprising a PCB card stack configuration, such as illustrated in FIG. 2, may comprise an air inlet 202 and an air outlet 204 each measuring about 90 mm (3.5 inches)×5 mm (0.2 inches). In various embodiments, such a photocatalytic system may measure about 117 mm (4.6 inches) in height, 135 mm (5.3 inches) in length, and 95 mm (3.7 inches) in width. These exemplary dimensions are not intended to be limiting in any way.

In various embodiments, the photocatalytic system 200 further comprises at least one ionizer 270 configured in an airflow channel prior to the inlet of the photocatalytic system 200. The ionizer 270 is configured to charge the various airborne pollutants 206 entering the system. In various embodiments, the ionizer 270 further comprises ESD needles 272 that discharge electrons (e−) that are picked up by the pollutants 206, thus becoming charged particles 208. The charged pollutant particles then enter the stack of cards where they encounter charged PCB cards. In particular, and as perhaps best seen in FIG. 3, each photoactivated semiconductor photocatalyst layer disposed on each PCB card is polarized, and thus the charged pollutant particles 208 are attracted specifically to the polarized photocatalyst layer, ensuring a residence time for the particle on the photocatalyst to react with the reductive and/or oxidative reactants present thereon. This aspect is particularly important for deactivating airborne virus particles, wherein the charged viral particles can attach to the polarized photocatalyst layer for a sufficient time for the biomolecules, such as RNA, to be denatured by the various reactive species present on the photocatalyst surface.

Figure 2:
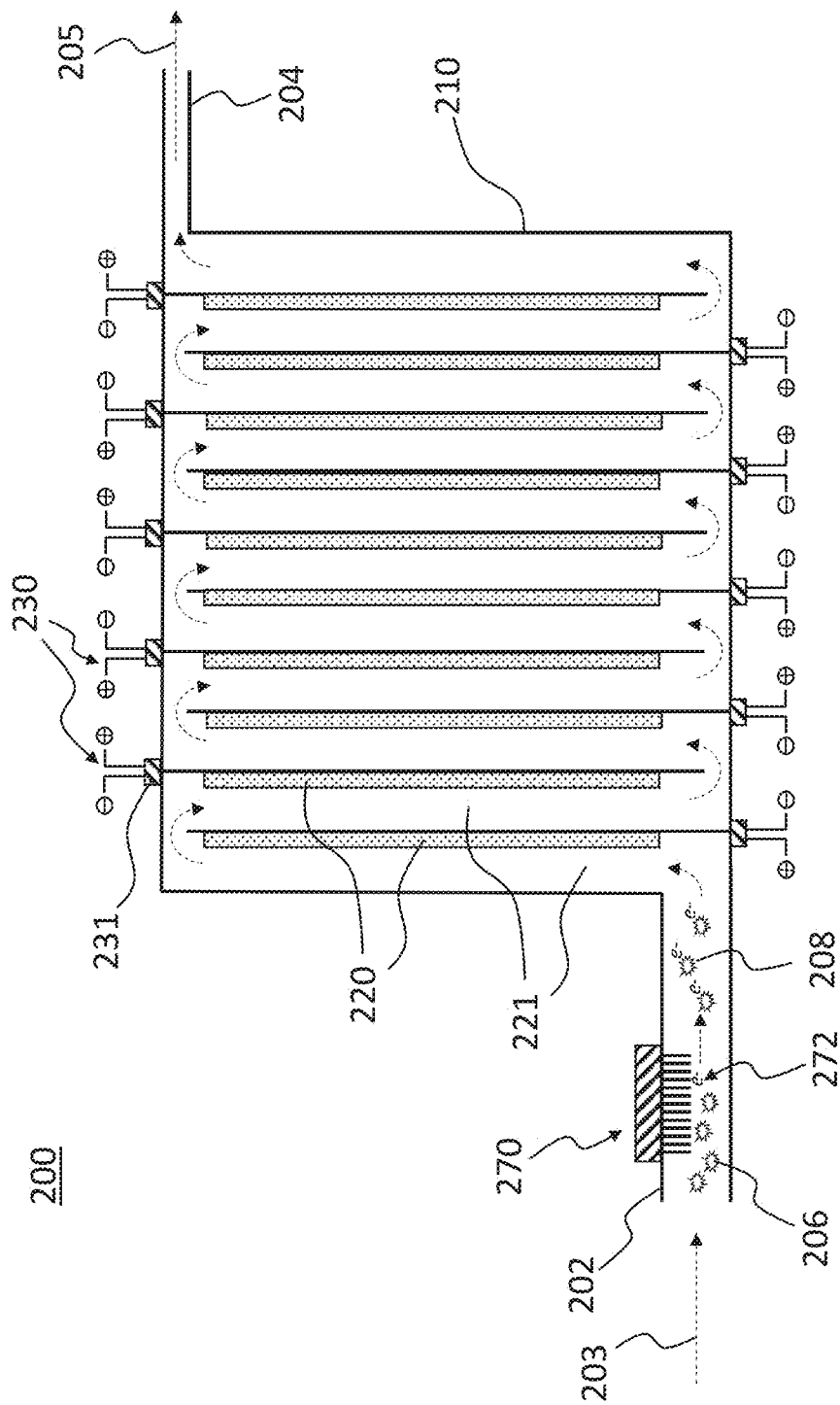
FIG. 2 illustrates an exemplary photoactivated semiconductor photocatalytic system further comprising a stack of PCB cards coated with a photoactivated semiconductor photocatalyst, wherein the PCB cards are arranged to form a serpentine-like airflow pathway through the photocatalytic system, in accordance with various embodiments.
Figure 3:
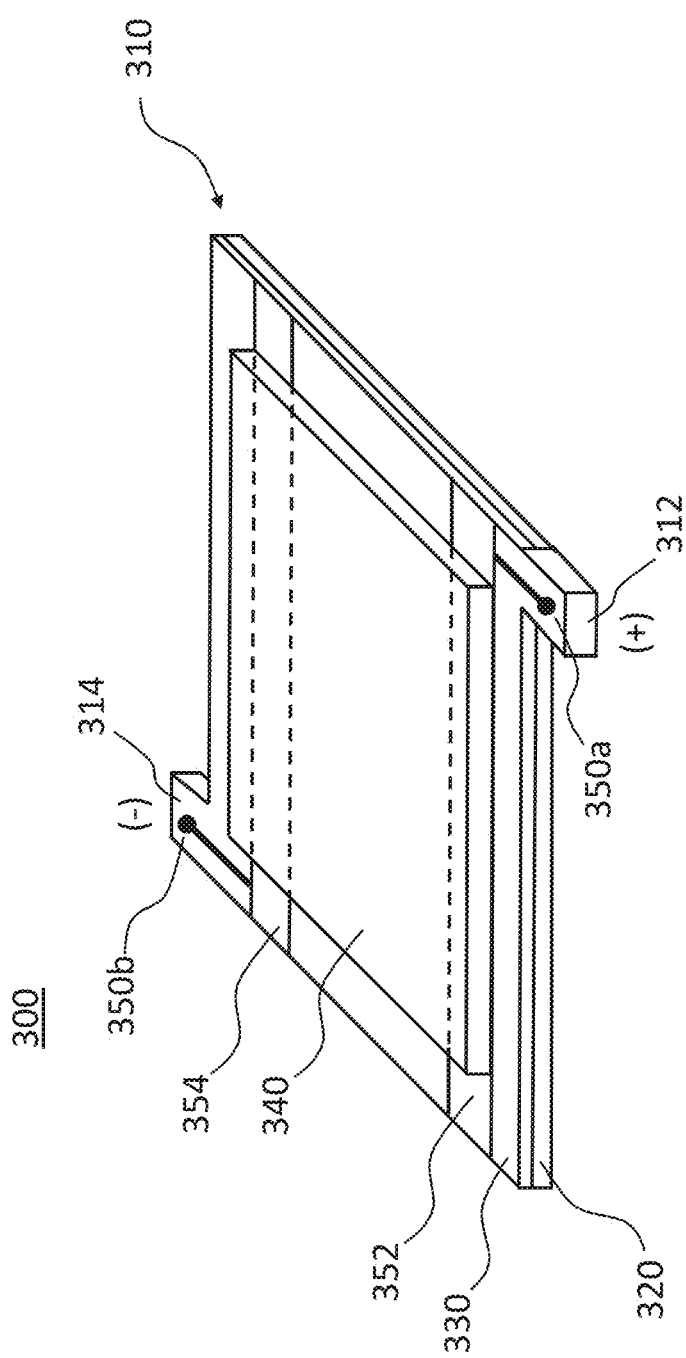
FIG. 3 illustrates an exemplary single PCB card comprising a layer of photoactivated semiconductor photocatalyst affixed to the PCB in accordance with various embodiments, wherein the PCB card further comprises electrodes for applying a potential.

FIG. 3 depicts a single exemplary PCB card 300, which in various embodiments, can be equivalent to one of the PCB cards 220 used in the photocatalytic system 200 illustrated in FIG. 2. An individual coated PCB card 300 comprises a PCB board 310 and a number of layers disposed on the PCB, each layer applied for example by a deposition process.

In FIG. 3, the PCB card 300 comprises a layer of photoactivated semiconductor photocatalyst 340 attached to the underlying substrate 320 via a cured adhesive 330. The board may further comprise two electrodes usable for connecting the PCB to a voltage source and polarizing the photoactivated semiconductor photocatalyst layer 340. In various embodiments, a positive electrode 352 and a negative electrode 354 are configured on the PCB such that the adhesive layer 330 and the photocatalyst layer 340 are overtop of the two electrodes. The two electrodes may be in any dimensional configuration, with the illustration showing the electrodes as thin conductive strips disposed parallel to one another on opposite ends of the PCB card.

In various embodiments, structural tabs 312 and 314 are configured on the PCB, such as in opposite corners, opposing edges, or even on the same edge. The tabs may be used to attach each PCB to an electrified frame, such as by plugging the tab into a corresponding slot configured in the frame. Each tab may further comprise the electrical contact, namely the positive contact 350a that connects to the positive electrode 352, and the negative contact 350b that connects to the negative electrode 354. The metal electrodes 352 and 354 may be deposited first on the substrate 320 by various lithographic methods, including a mask layer to mark off where the metal deposits are to go. In other embodiments, a PCB may begin with a uniform conducting layer, such as copper and the conducting layer masked off and then etched to leave behind the two electrode strips. In various embodiments, the substrate 320 of the PCB comprises Si, optionally with a $SiO_2$ layer. The electrodes 352/354 may comprise Pt, Pd, Ru, Ag, Ag, Cu, and so forth.

The base PCB 310 may comprise a simple layer single sided MCPCB with a metal base (Al, Cu, or Cu alloy), a dielectric layer, a copper circuit layer, IC components and a solder mask. In various embodiments, a chip-on-board COB MCPCB may be used. Such PCBs for use herein are available, for example, from Shenzhen JDB Technology Co., Ltd., Hangzhou, China.

To prepare a working PCB card for use in a PCB card stack, a photocatalyst layer is disposed on the PCB card that already includes the electrode strips (deposited thereon or formed by etching away the circuit layer everywhere except for the electrodes). As discussed herein above, many methods may be used to dispose a photocatalyst layer on a PCB card, such as via an adhesive disposed over the electrodes and the underlying substrate. An adhesive coated PCB may be exposed, for example, to a fog comprising water, surfactant, and photoactivated semiconductor photocatalyst mixture. The mixture rapidly condenses to create airborne photocatalyst impregnated water droplets that surround and embed into the adhesive layer 330 on the board 310. The resulting PCB card is then exposed to a curing process that hardens the adhesive to permanently capture and hold the photocatalyst layer 340 in place on the PCB card. In various embodiments, the photoactivated semiconductor photocatalyst in the fog comprises nanoparticles, with the nanoparticulate structure remaining in the finished photocatalyst layer 340. As mentioned and discussed above, many other methods may be used to form a layer of photocatalyst on a PCB card.

Each of the PCB cards 300 are then stacked in a frame by alternating attachment of an edge or two edges of each card to either a left frame or a right frame, so as to create the serpentine air flow path as per FIG. 2, and to electrify each board so that each photoactivated semiconductor photocatalytic layer is polarized. The two opposite sides of the frame can include a bus so that by plugging in an individual PCB card into the frame, the electrodes are connected up to the common line.

In practice, resistors at each board connection can be used so that the potential applied to each PCB card in the stack is different. In various embodiments, the potential may be lower or higher for each card sequentially through the stack in the direction of the airflow as needed. In various embodiments, certain PCB cards may have different potentials such that there is no cognizable gradient of potentials through the photocatalytic system of stacked PCB cards.

As illustrated in FIG. 2, pollutant particles 208, having been charged by the ionizer 270, will be attracted to the polarized PCB cards having the photoactivated semiconductor photocatalyst layers (340 in FIG. 3). This attraction (e.g., a negatively charged airborne pollutant attracted to the (+) side of a PCB card) results in a residence time for the particle on the catalyst layer sufficient for the reactive species present thereon to denature biomolecules in the particle, or otherwise destroy odoriferous molecules, and so forth. As mentioned, in practice, the PCB card is polarized by applying a potential to the card, but when charged particles attract to the polarized PCB card, the particles necessarily run into the photocatalytic layer disposed on the PCB card.

2. Photocatalytic System Comprising 3-DOM Structure or other Three-Dimensional Architecture In various embodiments, a photocatalytic system for use herein comprises a photoactivated semiconductor photocatalyst in a 3-DOM structure, such as an inverse opal. Stated another way, a preferred photocatalytic system comprises an inverse opal photoactivated semiconductor photocatalyst. Preparation of 3-DOM lattices was discussed herein above.

In various embodiments, the 3-DOM lattice may be 3D printed and then dip-coated and air blasted with the one or more photocatalysts such that the photoactivated semiconductor catalyst is sieved into and through the 3-DOM structure. The end result is a photoactivated semiconductor photocatalyst having a 3-dimensional structure.

Figure 4:
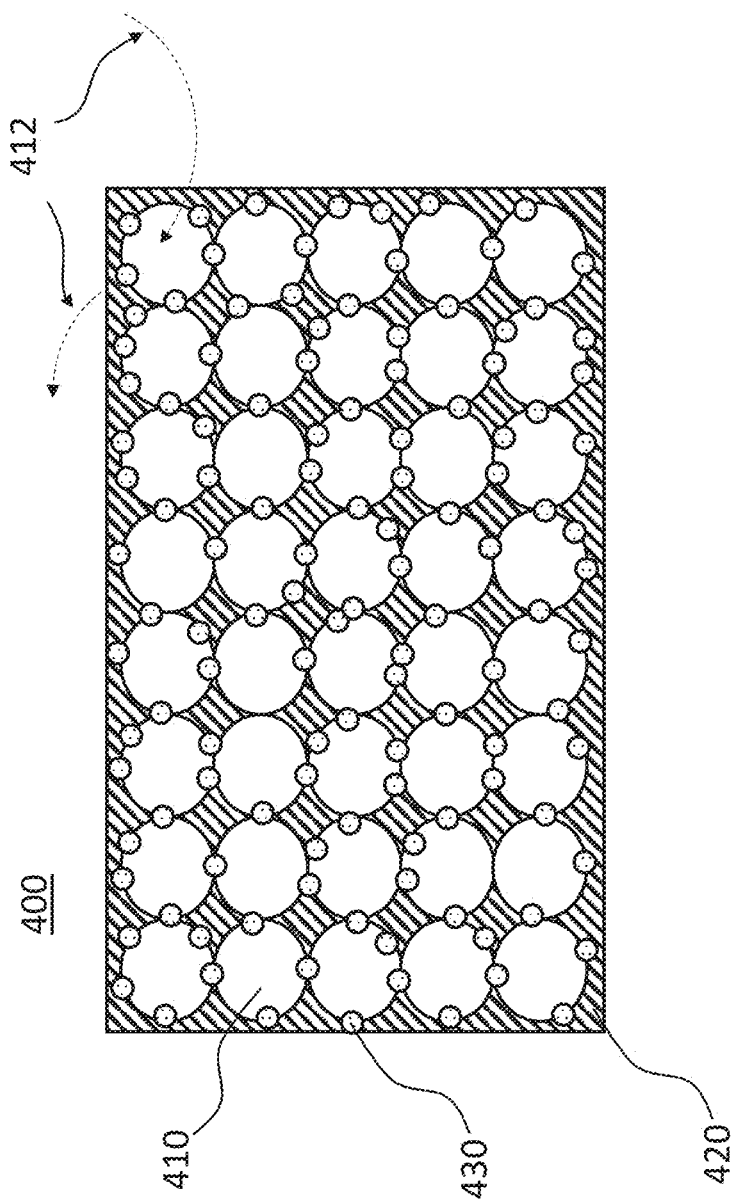
FIG. 4 illustrates an exemplary photocatalytic system comprising a photoactivated semiconductor photocatalyst having 3-DOM structure, in accordance with various embodiments.
Figure 5:
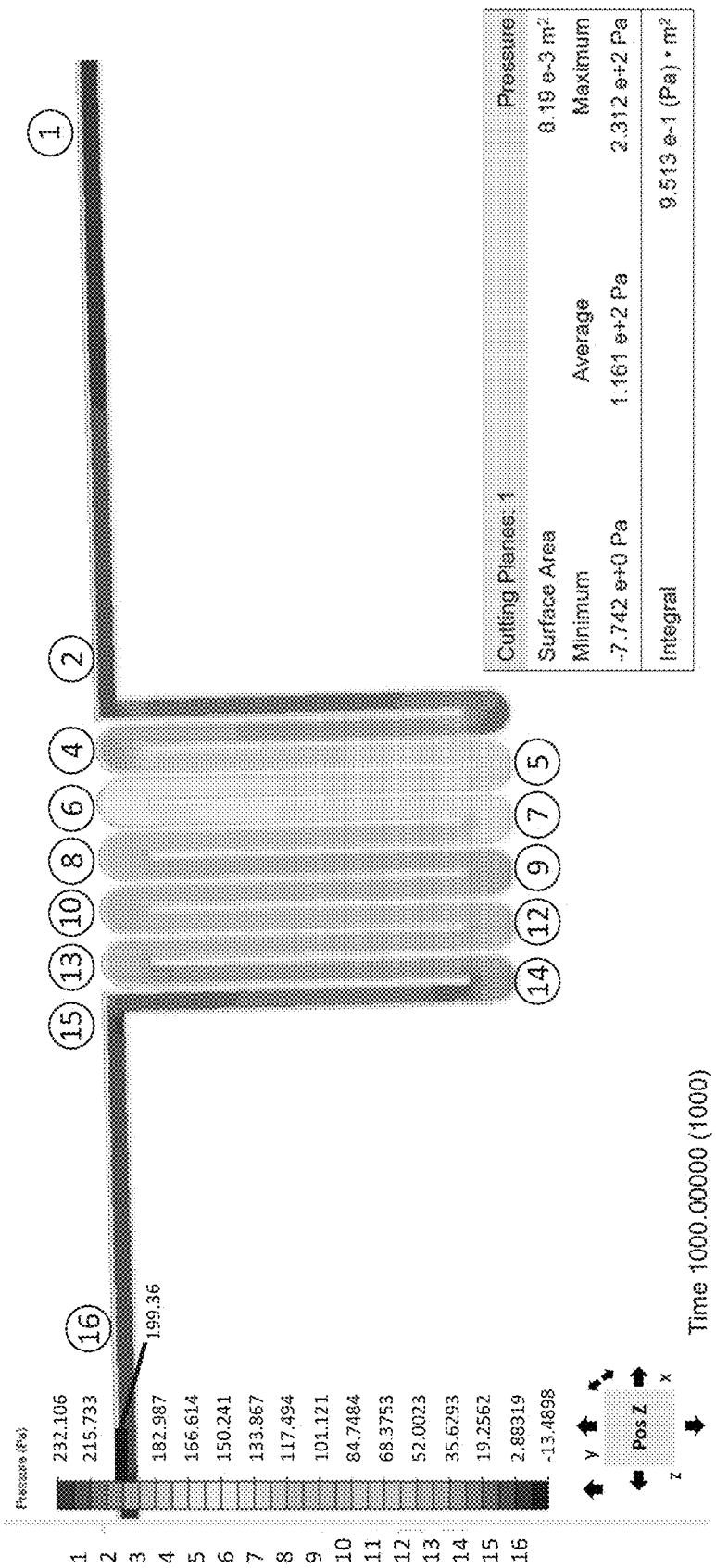
FIG. 5 illustrates pressure differences as air flows through a serpentine structure consisting of stacked PCB cards configured with 12 airflow channel segments, obtained in a simulation experiment. The simulation shows little head loss through the geometry of the card stack.

FIG. 4 illustrates an exemplary photocatalytic system 400 comprising a photoactivated semiconductor photocatalyst with a 3-DOM structure. The 3-DOM structure herein is essentially an open cell structure comprising holes 410 measuring from about 1 mm to about 5 mm in average diameter. The open cell structure provides pathways for air 412 to circulate through. In various embodiments, the lattice 420 itself may comprise a semiconductor photocatalytic material. In various embodiments, the lattice 420 may comprise a single semiconductor photocatalyst embedded in a resin matrix, or an intimate mixture of more than one semiconductor photocatalyst. In other embodiments, the lattice 420 comprises only one components of a two-component photoactivated semiconductor system, and the other component in the photoactivated semiconductor photocatalyst system appears as particles 430 (e.g., nanoparticles, crystals, or amorphous particle) within the architecture, such as adhered to lattice surfaces. In still further embodiments, the lattice 420 may comprise only a lattice material having no photocatalytic properties, like a resin, and the particles 430 comprise the one or more semiconductor photocatalysts present in the photoactivated semiconductor photocatalytic system.

3. Photocatalytic System Comprising a Combination of PCB Card Stack and 3-DOM Structure In various embodiments, a photocatalytic system for use herein comprises both a PCB card stack as discussed above in Part 1 and a 3-DOM structure in combination. In various embodiments, the 3-DOM lattice structure creates "tripping turbulence" for the contaminated air entering the PCB card stack.

In various embodiments, the 3-DOM lattice trips turbulence by acting like a filter prior to entering the PCB card stack. Although the diameter of the holes in the 3-DOM lattice may vary (e.g., from 1 mm to about 5 mm), the 3-DOM lattice can be positioned such that it directs light in a particular direction. In various embodiments, ESD needles of an ionizer may be used to create turbulence in addition to charging the particulate pollutants prior to entering the PCB card stack.

II. Methods of Air Purifier—General Aspects

In various embodiments, the present disclosure includes methods of air purification. In various embodiments, methods of air purification utilize an air purifier in accordance with the present disclosure. The methods also provide air decontamination, air deodorization, air cleaning, air filtering, and air sanitizing, depending on the nature of the contaminants present in the air requiring purification.

The method generally comprises placing contaminated air into contact with a photoactivated semiconductor photocatalyst irradiated with incident radiation configured to excite the photoactivated semiconductor photocatalyst. The photoactivated semiconductor photocatalyst may be part of a photocatalytic system comprising additional features that may physically support the photoactivated semiconductor photocatalyst or make it more efficient, such as by increasing the probability the contaminated air, and the airborne contaminants therein, contact the photoactivated semiconductor photocatalyst.

In various embodiments, a method of air purification comprises placing contaminants present in the air into contact with a surface of a photoactivated semiconductor photocatalyst irradiated with incident radiation configured to excite the at least one component therein and generate reductive and/or oxidative reactive species from at least one of oxygen or water to destroy or deactivate the contaminants. In various embodiments, reactive species generated on the photoactivated semiconductor photocatalyst comprise at least one of hydrogen peroxide ($H_2O_2$), hydroperoxyl radical ($HO_2 \cdot$), hydroxide anion ($HO^-$), hydroperoxyl radical anion ($HO_2 \cdot^-$), hydroxyl radical ($HO \cdot$), hydronium ion ($H_3O+$) or superoxide radical anion ($\cdot O_2^-$).

In various embodiments, the airborne contaminants present in the air include inanimate pollutants and microorganisms. In various embodiments, the airborne inanimate pollutants include, but are not limited to, dust, smoke, grease, oils, ashes, hair, skin dander, odoriferous molecules such as amines and thiols, and pollen. In various embodiments, airborne microorganisms include, but are not limited to, airborne bacteria, viruses, molds, yeasts and spores. In various embodiments, contaminated air comprises both microorganisms and the odors they produce.

In various embodiments, hydrogen peroxide ($H_2O_2$), hydroperoxyl radical ($HO_2 \cdot$), hydroxide anion ($HO^-$), hydroperoxyl radical anion ($HO_2 \cdot^-$), hydroxyl radical ($HO \cdot$), hydronium ion ($H_3O+$) and/or superoxide radical anion ($\cdot O_2^-$) generated from oxygen and/or water present on the surface of the photoactivated semiconductor photocatalyst are capable of reducing/oxidizing organic molecules such as amines and thiols to convert odoriferous substances into odorless molecules. In various embodiments, organic molecules are reductively or oxidatively cleaved by the air purification methods herein.

In various embodiments, hydrogen peroxide ($H_2O_2$), hydroperoxyl radical ($HO_2 \cdot$), hydroxide anion ($HO^-$), hydroperoxyl radical anion ($HO_2 \cdot^-$), hydroxyl radical ($HO \cdot$), hydronium ion ($H_3O+$) and/or superoxide radical anion ($\cdot O_2^-$) thus generated from oxygen and/or water present on the surface of the photoactivated semiconductor photocatalyst are capable of reducing/oxidizing organic molecules and biopolymers such as RNA, DNA and proteins, resulting in the destruction or deactivation of airborne and living bacteria, viruses, molds, yeasts and spores.

In various embodiments, a photoactivated semiconductor photocatalytic used in the methods of air purification herein comprises at least one semiconductor photocatalyst as defined herein above.

Methods of air purification may be performed by using an air purifier in accordance with the present disclosure. As discussed herein, an air purifier in accordance with various embodiments comprises: a photocatalytic system comprising a photoactivated semiconductor photocatalyst; and a lamp configured to irradiate the photoactivated semiconductor photocatalyst with incident radiation configured to excite the photoactivated semiconductor photocatalyst, wherein the photocatalyst system is configured to generate at least one of hydrogen peroxide ($H_2O_2$), hydroperoxyl radical ($HO_2 \cdot$), hydroxide anion ($HO^-$), hydroperoxyl radical anion ($HO_2 \cdot^-$), hydroxyl radical ($HO \cdot$), hydronium ion ($H_3O+$) or superoxide radical anion ($\cdot O_2^-$) from oxygen and/or water present on the photoactivated semiconductor photocatalyst.

In various embodiments, a method of purifying contaminated air comprises conveying the contaminated air into an air purifier, the air purifier comprising (i) a photocatalytic system further comprising a photoactivated semiconductor photocatalyst and (ii) a lamp configured to irradiate and excite the photoactivated semiconductor photocatalyst with incident radiation, wherein contaminants present in the contaminated air contact a surface of the photoactivated semiconductor photocatalyst, wherein the photocatalyst system is configured to generate to generate at least one of hydrogen peroxide ($H_2O_2$), hydroperoxyl radical ($HO_2 \cdot$), hydroxide anion ($HO^-$), hydroperoxyl radical anion ($HO_2 \cdot^-$), hydroxyl radical ($HO \cdot$), hydronium ion ($H_3O+$) or superoxide radical anion ($\cdot O_2^-$) from oxygen and/or water present on the photoactivated semiconductor photocatalyst, destroying, denaturing or deactivating the contaminants.

In various embodiments, a method of purifying contaminated air comprises deactivating airborne single-stranded virus particles, including SARS-CoV-2.

In various embodiments, a method purifying contaminated air further comprises positively or negatively charging airborne contaminants so that the charged contaminants are attracted by electromotive forces to various+/−charged features in a photocatalytic system. This attraction ensures sufficient contact time between the charged contaminant particles and the charged features within the photocatalytic system for the reductive and/or oxidative reactant species in the photocatalytic system to reduce, oxidize, deodorize, deactivate and/or destroy the airborne contaminants.

III. Simulation Experiment Through PCB Card Stack

FIG. 5 sets forth the results of a simulation experiment. The simulation used a PCB card stack having eleven (11) PCB cards stacked such that a serpentine airflow path comprised twelve (12) parallel airpath channels. The simulation results highlight the control of turbulence while minimizing the loss of pressure. This can be interpreted as minimal heat loss, and other geometries may be considered. In the illustration, numbers 1-16 are assigned as a guide for the reader to interpret the shading on the serpentine airflow diagram. The diagram shows bars of pressure in each of the air channels between the PCB cards in the stack, and at the inlet and outlet.

IV. Functional Design Configured for Incorporation within an HVAC System

In various embodiments, an air purifier in accordance with the present disclosure, comprising a prefilter, particle ionizer, UV light, and UV activated photocatalytic system is adapted for incorporation inside an HVAC unit. An air purifier configured for use inside an HVAC system may be passive, in that there is no need for a fan or blower within the air purifier itself (e.g., no need for fan 120 in FIG. 1). An air purifier configured for HVAC systems can be an inline system, meaning that the air purifier airflow direction would align parallel to the airflow through the HVAC system.

Though an inline air purifier in accordance with the present disclosure can either precede or follow existing coils or air handlers in the HVAC system, the resulting airflow from the air purifier unit will depend on the existing air handler present in the HVAC system.

Figure 6A:
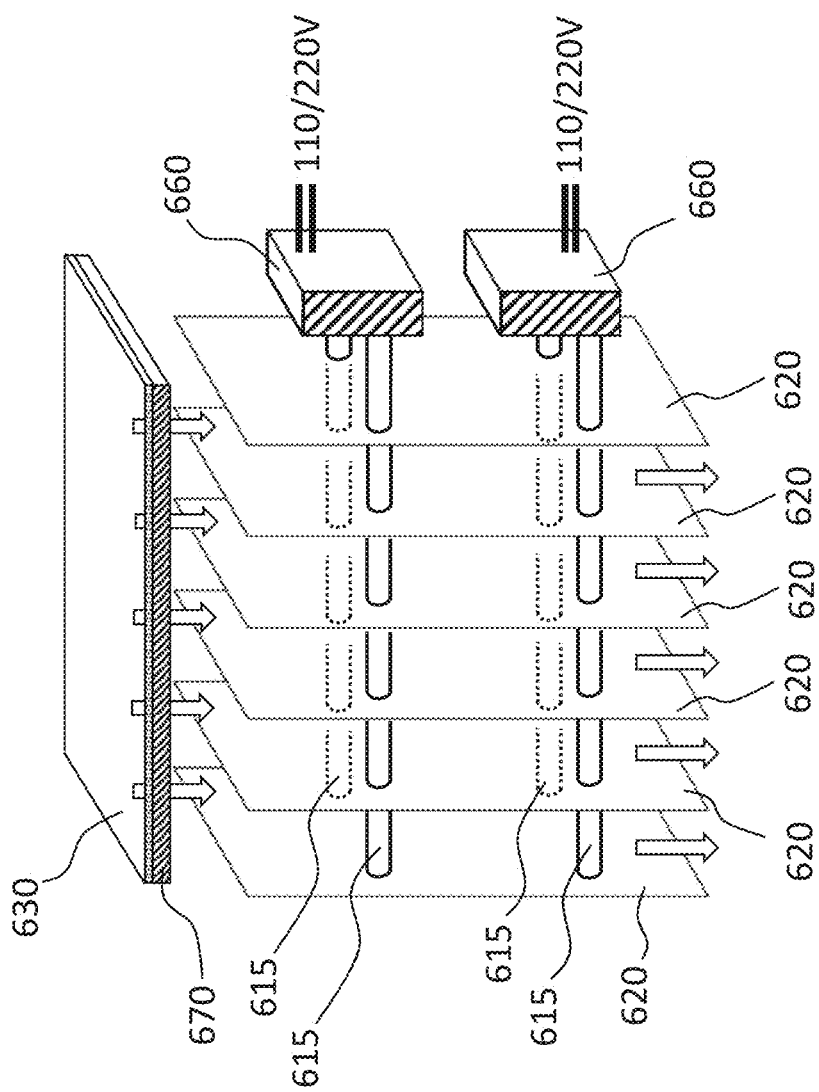
FIG. 6A illustrates a perspective view of a functional design for use in an HVAC system.

With reference now to FIGS. 6A and 6B, the air purifier unit employs the shape of a cube/rectangular prism, with the exact dimensions dependent upon, for example, square footage constraints. In FIGS. 6A/6B, any necessary framing is not shown for the sake of clarity, with the assumption the functional design depicted can be held together with a simple angle iron (or aluminum) framing. FIG. 6A illustrates a perspective view of the functional design whereas FIG. 6B illustrates a front plan view of the same functional design for use in an HVAC system. In both FIGS. 6A/6B, the block arrows represent airflow direction through the air purifier unit.

Air purification within an HVAC system begins with a prefilter 630, such as a filter having a MERV 11 or MERV 13 rating, configured to remove larger particles in order to maximize the sanitizing efficacy levels on the photocatalytic reactors, which would otherwise fowl with particulates. This efficiency is brought forward by the fact that in the fixed amount of surface area within the photocatalytic coated panels 620, more reduction reactions can occur if the average particle size remaining within the unit after ionization is smaller. The prefilter may be constructed with various materials as described herein above. Following the prefilter, there is a negative (−) or positive (+) ion generator 670 that precedes the coated panels 620. The ion generator 670 is intended to negatively or positively charge particles within the incoming air volume before they reach the coated panels, as described in detail herein above. Again, this ionization should allow particles to gain an affinity to become attracted to either other particles and fall from the airflow, or to the photocatalyst coated panels 620, again maximizing the number instances for photocatalysis to occur. After the ion generator 670 is the array of panels 620 placed in an upright position parallel to the air flow, with the arrangement intended to minimize impact to the system pressure. It is important to note that this parallel panel arrangement differs from the staggered stack arrangement in FIG. 2 that creates a serpentine airflow pathway. In the configuration with parallel panels, e.g., as illustrated in FIGS. 6A/6B, there is less restricted airflow so as not to lessen the efficiency of the HVAC system. Depending on the configuration of the photocatalytic system, the unit may comprise from about 6 to about 20 photocatalyst coated panels. These panels may comprise, for example, fiberglass, plastic, solid metal such as galvanized steel or aluminum, or a metal mesh, and may optionally be constructed of the same material as the framing/housing of the air purifier, or the panels may be constructed of cardboard or a thin lightweight wood encased in a metal foil, such as an aluminum foil sleeve. The choice of materials for the panels and sleeves (if present) may be based on the need to polarize the panels so that they attract electrically charged pollutant particles. The panels 620 may be held in place by tracks and/or brackets and are coated in at least one of the photocatalyst mixtures described herein above. The air handler of the HVAC system powers the airflow through the air purifier unit and, in particular, between adjacent panels 620 that provide an airflow channel colinear with the airflow pathway of the HVAC system.

By following the air flow, the time over which the attraction from particles to panels 620 occurs is maximized, again increasing the amount of sanitizing reactions occurring on the surface of the panels 620. Orthogonal (or at another angle) to these plates 620 are tubular UV bulbs 615, which pass through apertures cut through each of the panels 620, the light tubes optionally attached to side walls or framing on the air purifier. The UV light tubes 615 may fit directly into suitably dimensioned holes and grommets provided on power supply units 660 that, in various embodiments, also help support the long light tubes in addition to providing the necessary voltage (110 or 220V, for example) to power the light tubes. In addition to providing the sanitizing power of UV-C radiation, the bulbs 615 irradiate the photocatalyst applied on the panels 620 to provide the activation energy for the reductive photocatalytic reactions described herein above. To counterbalance the limited radius in which irradiation is effective, the UV-C bulbs 615 in various model variants will have an arrangement to ensure the highest number of particles are irradiated and that the entirety of the photocatalyst on the surface area of the panels 620 will be activated.

The number of bulbs 615 is another functional design aspect that can vary between design variants, as the smallest variant can use, for example, twelve (12) UV-C bulbs and a largest design variant can use, for example, twenty (20) bulbs. In model versions where photocatalytic panels 620 are made entirely of aluminum, the last element in the reaction chamber will be a charge applied to the photocatalyst-coated panels. A small current at a relatively low voltage will be applied to the array of panels 620, with a resistor between each panel causing each successive panel to reach a lower voltage than its preceding panel, as discussed previously. This charging of the panels further intensifies the attraction between the particles in the unit and the photocatalytic panels, again increasing the number of reductive reactions and thus the efficiency of the entire unit.

An air purifier unit such as illustrated in FIG. 6A/6B may be configured to support servicing efficiency. Although not illustrated, various designs features make use of two plates constituting the bottom base of the unit. The plates move relative to one another. The first base plate is a part of the external skeleton of the photocatalytic system, and, as such, acts as the support or the base for the unit. Positioned above the external bottom base plate is a system of wooden, plastic or metal dowels configured as rollers to allow for the second base plate to move. The second base plate, placed on the dowels, will house all the air purification technology stated prior, except for the prefilter 630 that will be placed before a detachable part of the photocatalytic reactor. Specifically, the second base plate serves as the bottom panel of the enclosed reactor section through which the air volume will flow.

To service the photocatalytic reactor components, this second base plate will have the capacity to slide out of the side of the external housing of the unit, allowing easy access to remove the photocatalytic panels 620 and bulbs 615. Before sliding out the top base plate, the UV-C bulbs will have to be disconnected from their sockets, which are positioned immediately outside the front and back panels of the external unit housing and accessible by unlatching a hinged cap on the front of the unit. Once the bulbs have been unplugged and the base plate has been rolled out, the panels can be removed by pulling them vertically from their position held by either the tracks or brackets. In various embodiments, the prefilter can also be modular by having a small latching section that makes for easy maintenance and replacement.

In the detailed description, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected, coupled or the like may include permanent (e.g., integral), removable, temporary, partial, full, and/or any other possible attachment option. Any of the components may be coupled to each other via friction, snap, sleeves, brackets, clips or other means now known in the art or hereinafter developed. Additionally, any reference to without contact (or similar phrases) may also include reduced contact or minimal contact.

Benefits, other advantages, and solutions to problems have been described with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

All structural, chemical, and functional equivalents to the elements of the above-described various embodiments that are known to those of ordinary skill in the art are expressly incorporated by reference and are intended to be encompassed by the present claims. Moreover, it is not necessary for an apparatus or component of an apparatus, or method in using an apparatus to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises", "comprising", or any other variation thereof, are intended to cover a non-exclusive inclusion, such that a chemical, chemical composition, process, method, article, or apparatus that comprises a list of elements does not include only those elements but may include other elements not expressly listed or inherent to such chemical, chemical composition, process, method, article, or apparatus.

The invention claimed is:

1. An air purifier comprising:
    a photocatalytic system comprising a series of parallel panels, each panel coated with at least one photoactivated semiconductor photocatalyst; and
    at least one lamp configured to irradiate the photoactivated semiconductor photocatalyst present on each of the parallel panels with incident radiation configured to excite the photoactivated semiconductor photocatalyst,
    wherein the photocatalyst system is configured to generate at least one reductive or oxidative reactive species in the presence of at least one of oxygen or water in contact with the photoactivated semiconductor photocatalyst, and
    wherein the at least one photoactivated semiconductor photocatalyst has an energy bandgap ($E_g$) of from about 12.4eV to about 1.24meV, referenced to NHE.

2. The air purifier of claim 1, wherein the at least one reductive or oxidative reactive species comprises at least one of hydrogen peroxide ($H_2O_2$), hydroperoxyl radical ($HO_2\cdot$), hydroxide anion ($HO^-$), hydroperoxyl radical anion ($HO_2\cdot^-$), hydroxyl radical ($HO\cdot$), hydronium ion ($H_3O+$) and/or superoxide radical anion ($\cdot O_2^-$).

3. The air purifier of claim 1, wherein the incident radiation has an energy ($E_s$), wherein $E_s \geq E_g$ of the at least one photoactivated semiconductor photocatalyst.

4. The air purifier of claim 1, wherein the photocatalytic system comprises two photoactivated semiconductor photocatalysts having overlapping, non-overlapping, or offset bandgaps, wherein each bandgap is from about 12.4eV to about 1.24meV, referenced to NHE.

5. The air purifier of claim 1, wherein the at least one photoactivated semiconductor photocatalyst is modified by at least one of coupling to an electron transport layer (ETL) material, coupling to a hole transport layer (HTL) material, doping, surface modification, or any combination thereof.

6. The air purifier of claim 1, wherein the at least one photoactivated semiconductor photocatalyst comprises an elemental material, metal chalcogenide, metal oxide, metal oxyhalide, metal phosphate, metal hydroxide, metal nitride, metal molybdate, metal vanadate, or metal tungstate, wherein the metal is Ti, C, Cr, Mn, Fe, Co, Ni, Cu, Zn, Ga, Zr, Nb, Mo, Tc, Ru, Rh, Pd, Ag, Cd, In, Hf, Ta, W, Re, Os, Ir, Pt, Au, Hg or Tl.

7. The air purifier of claim 6, wherein the at least one photoactivated semiconductor photocatalyst is selected from the group consisting of $Bi_2Mo_3O_{12}$, $Bi_2Mo_2O_9$, $Bi_2MoO_6$, $BiVO_4$, $Bi_2WO_6$, BiOBr, BiOI, $MoS_2$, CuO, $Cu_2O$, $MoO_3$, $WO_3$, $BiPO_4$, $Ag_3PO_4$, $TiO_2$, $SnO_2$, $InVO_4$, $FeVO_4$, $Ag_4V_2O_7$, $Fe_3O_4$, and mixtures thereof.

8. The air purifier of claim 1, wherein the photocatalytic system comprises two photoactivated semiconductor photocatalysts consisting of $Bi_2MoO_6$ and $Ag_3PO_4$.

9. The air purifier of claim 1, wherein the lamp comprises a low pressure mercury vapor lamp having a tubular shape, the at least one lamp configured orthogonal to the series of parallel panels and passing through apertures configured in each panel, the lamp configured to radiate UV-C incident electromagnetic radiation at a wavelength of about 254 nm.

10. The air purifier of claim 1, wherein the series of parallel panels comprise from about 12 individual panels to about 20 individual panels.

11. The air purifier of claim 10, wherein each panel in the series of parallel panels is bipolarized with an applied electrical potential.

12. The air purifier of claim 1, further comprising an ionizer configured to negatively or positively charge airborne contaminants in an airflow pathway leading between adjacent panels in the series of parallel panels.

13. The air purifier of claim 1, further comprising an ozone trap configured to remove ozone generated from the photocatalytic system, the lamp or the combination thereof.

14. A method of destroying or deactivating airborne contaminants present in contaminated air flow in an HVAC system, the method comprising:
  contacting the contaminants present in the contaminated air with surfaces of a photoactivated semiconductor photocatalyst coated on a series of parallel panels and irradiated with incident radiation configured to excite the photoactivated semiconductor,
  wherein irradiation of the photoactivated semiconductor photocatalyst generates reductive and/or oxidative reactive species from at least one of oxygen or water present on the surface of the photoactivated semiconductor photocatalyst,
  wherein the reductive and/or oxidative reactive species thus generated destroy or deactivate the airborne contaminants, and
  wherein the at least one photoactivated semiconductor photocatalyst has an energy bandgap ($E_g$) of from about 12.4eV to about 1.24meV, referenced to NHE.

15. The method of claim 14, wherein the reductive and/or oxidative reactive species generated comprise at least one of hydrogen peroxide ($H_2O_2$), hydroperoxyl radical ($HO_2·$), hydroxide anion ($HO^-$), hydroperoxyl radical anion ($HO_2·^-$), hydroxyl radical ($HO·$), hydronium ion ($H_3O+$) or superoxide radical anion ($·O_2^-$).

16. The method of claim 14, wherein irradiation of the photoactivated semiconductor photocatalyst further comprises irradiation with incident radiation of having an energy ($E_s$) greater than or equal to a bandgap energy ($E_g$) of the at least one photoactivated semiconductor photocatalyst.

17. The method of claim 14, wherein contacting the contaminants present in the contaminated air with surfaces of a photoactivated semiconductor photocatalyst coated on a series of parallel panels further comprises conveying the contaminated air between adjacent panels in the series of parallel panels by an air handler of the HVAC system.

18. The method of claim 14, further comprising positively or negatively charging the contaminants in the contaminated air prior to the contaminants coming into contact with surfaces of the photoactivated semiconductor photocatalyst.

19. The method of claim 18, further comprising applying an electrical potential to each of the panels in the series of parallel panels such that an electric/electromagnetic field thus produced around each panel attracts charged contaminants to surfaces of the photoactivated semiconductor photocatalyst.

20. The method of claim 14, wherein destroying or deactivating the contaminants further comprises destroying or deactivating an airborne microorganism.

21. The method of claim 14, wherein destroying or deactivating the contaminants further comprises deactivating an airborne single-stranded RNA virus particle.

22. The method of claim 21, wherein the deactivating of the airborne single-stranded RNA virus particle further comprises contacting the airborne single-stranded RNA virus particle with a surface of the photoactivated semiconductor photocatalyst for a time sufficient for the reductive and/or oxidative reactive species thus generated to denature a biomolecule present in the single-stranded RNA virus particle.

23. The method of claim 14, wherein the contaminates contaminants include airborne SARS-CoV-2 virus particles.

24. An air purifier comprising:
  a photocatalytic system comprising a series of parallel panels, each panel coated with at least one photoactivated semiconductor photocatalyst and each panel bipolarized with an applied electrical potential; and
  at least one lamp configured to irradiate the photoactivated semiconductor photocatalyst present on each of the parallel panels with incident radiation configured to excite the photoactivated semiconductor photocatalyst,
  wherein the photocatalyst system is configured to generate at least one reductive or oxidative reactive species in the presence of at least one of oxygen or water in contact with the photoactivated semiconductor photocatalyst.

25. The air purifier of claim 24, further comprising an ionizer configured to negatively or positively charge airborne contaminants in an airflow pathway leading between adjacent panels in the series of parallel panels such that an electric/electromagnetic field thus present around each panel attracts negatively or positively charged airborne contaminants to surfaces of the photoactivated semiconductor photocatalyst.

* * * * *

UNITED STATES PATENT AND TRADEMARK OFFICE
CERTIFICATE OF CORRECTION

PATENT NO. : 11,623,018 B2
APPLICATION NO. : 17/220768
DATED : April 11, 2023
INVENTOR(S) : Devon Paul Scheg et al.

It is certified that error appears in the above-identified patent and that said Letters Patent is hereby corrected as shown below:

In the Claims

At Column 30, Line 31, in Claim 23, please delete "contaminates"

Signed and Sealed this
Twenty-third Day of May, 2023

*Katherine Kelly Vidal*

Katherine Kelly Vidal
*Director of the United States Patent and Trademark Office*